United States Patent
Monson et al.

(10) Patent No.: US 12,285,375 B2
(45) Date of Patent: Apr. 29, 2025

(54) WIRELESS POWER DISTRIBUTION IN PATIENT SUPPORT SURFACE

(71) Applicant: Hill-Rom Services, Inc., Batesville, IN (US)

(72) Inventors: Gavin M. Monson, Oxford, OH (US); Frank Sauser, Cincinnati, OH (US); Douglas A. Seim, Okeana, OH (US)

(73) Assignee: Hill-Rom Services, Inc., Batesville, IN (US)

( * ) Notice: Subject to any disclaimer, the term of this patent is extended or adjusted under 35 U.S.C. 154(b) by 362 days.

(21) Appl. No.: 17/708,100

(22) Filed: Mar. 30, 2022

(65) Prior Publication Data

US 2022/0313517 A1    Oct. 6, 2022

Related U.S. Application Data

(60) Provisional application No. 63/168,520, filed on Mar. 31, 2021.

(51) Int. Cl.
*A61G 7/057*    (2006.01)
*A61B 5/00*    (2006.01)
(Continued)

(52) U.S. Cl.
CPC ........ *A61G 7/05769* (2013.01); *A61B 5/0205* (2013.01); *A61B 5/6892* (2013.01);
(Continued)

(58) Field of Classification Search
CPC ............ A61G 7/05769; A61G 7/05784; A61G 2203/10; A61G 2203/32; A61G 2203/34;
(Continued)

(56) References Cited

U.S. PATENT DOCUMENTS

| 7,722,375 B2 | 5/2010 | Hagen et al. |
| 9,106,203 B2 | 8/2015 | Kesler et al. |
| 9,337,901 B2 | 5/2016 | Takahashi |

(Continued)

FOREIGN PATENT DOCUMENTS

CN    208423945 U    1/2019

OTHER PUBLICATIONS

Park, et al., "Recent Progress in Wireless Sensors for Wearable Electronics", MDPI, Sensors, Oct. 9, 2019, vol. 19, Issue 20, pp. 1-34.

*Primary Examiner* — Jonathan T Kuo
(74) *Attorney, Agent, or Firm* — Price Heneveld LLP

(57) ABSTRACT

A patient support apparatus includes a frame having a supporting surface. A transmitting element is coupled to the frame. A surface assembly is selectively positioned on the supporting surface. The surface assembly includes a surface selectively enclosing an interior. A controller is communicatively coupled to the transmitting element. A sensor assembly is coupled to the surface assembly. The sensor assembly includes a sensor configured to sense information about at least one of the surface assembly and a person positioned on the surface assembly. A receiving assembly is operably coupled to the surface assembly and the sensor assembly. The receiving assembly is configured to selectively interact with the transmitting element via a charging interface to power the sensor assembly.

18 Claims, 23 Drawing Sheets

(51) Int. Cl.
*A61B 5/0205* (2006.01)
*H02J 50/10* (2016.01)

(52) U.S. Cl.
CPC .......... *A61G 7/05784* (2016.11); *H02J 50/10* (2016.02); *A61G 2203/10* (2013.01); *A61G 2203/32* (2013.01); *A61G 2203/34* (2013.01); *A61G 2203/46* (2013.01); *A61G 2210/70* (2013.01)

(58) Field of Classification Search
CPC ........... A61G 2203/46; A61G 2210/70; A61B 5/0205; A61B 5/6892; H02J 50/10
See application file for complete search history.

(56) References Cited

U.S. PATENT DOCUMENTS

| | | | |
|---|---|---|---|
| 9,722,447 B2 | 8/2017 | Partovi | |
| 10,027,179 B1 | 7/2018 | Bello et al. | |
| 10,561,551 B2* | 2/2020 | Lambarth | H02J 7/00034 |
| 10,568,513 B2* | 2/2020 | Lee | H04B 17/318 |
| 10,818,163 B2 | 10/2020 | Huster | |
| 10,945,679 B2* | 3/2021 | Baker | A61B 5/6891 |
| 11,424,646 B2* | 8/2022 | Holmvik | A47C 21/044 |
| 2015/0057653 A1 | 2/2015 | Sugiyama | |
| 2016/0158083 A1* | 6/2016 | Lambarth | A61G 3/0254 5/600 |
| 2016/0217672 A1* | 7/2016 | Yoon | A61B 5/4818 |
| 2016/0248276 A1 | 8/2016 | Hong et al. | |
| 2018/0214091 A1* | 8/2018 | Baker | A61G 7/018 |
| 2018/0256030 A1* | 9/2018 | Lee | H04B 17/318 |
| 2019/0229559 A1 | 7/2019 | Boccoleri et al. | |
| 2020/0006988 A1 | 1/2020 | Leabman | |
| 2020/0336010 A1* | 10/2020 | Holmvik | A47C 27/083 |
| 2023/0165743 A1* | 6/2023 | Monson | H02J 50/90 601/55 |

* cited by examiner

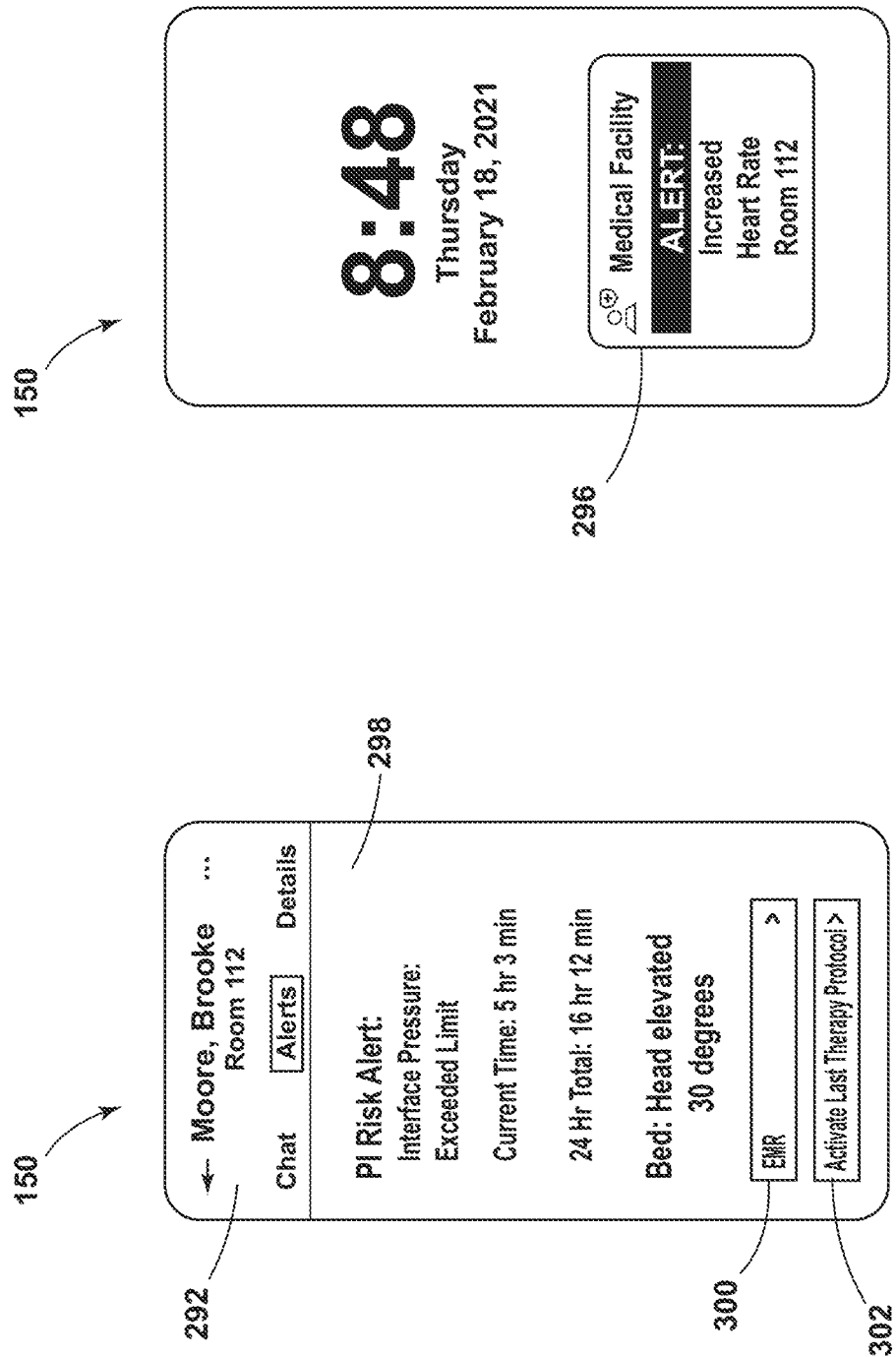

WIRELESS POWER DISTRIBUTION IN PATIENT SUPPORT SURFACE

CROSS-REFERENCE TO RELATED APPLICATION

This application claims priority to U.S. Provisional Patent Application No. 63/168,520, filed on Mar. 31, 2021, entitled "WIRELESS POWER DISTRIBUTION IN PATIENT SUPPORT SURFACE," the disclosure of which is hereby incorporated herein by reference in its entirety.

FIELD OF THE DISCLOSURE

The present disclosure generally relates to wireless power distribution, and more particularly to wireless power distribution in or near a patient support surface.

SUMMARY OF THE DISCLOSURE

According to one aspect of the present disclosure, a patient support apparatus includes a frame having a supporting surface. A transmitting element is coupled to the frame. A surface assembly is selectively positioned on the supporting surface. The surface assembly includes a surface selectively enclosing an interior. A controller is communicatively coupled to the transmitting element. A sensor assembly is coupled to the surface assembly. The sensor assembly includes a sensor configured to sense information about at least one of the surface assembly and a person positioned on the surface assembly. A receiving assembly is operably coupled to the surface assembly and the sensor assembly. The receiving assembly is configured to selectively interact with the transmitting element via a charging interface to power the sensor assembly.

According to another aspect of the present disclosure, a charging system for a medical facility includes a support apparatus having a frame and a siderail. The frame has a supporting surface. A surface assembly is selectively positioned on the supporting surface. A transmitting element is coupled to at least one of the frame and the siderail. A sensor assembly includes a biometric sensor that is configured to obtain biometric data of a person supported on the surface assembly. A receiving assembly is operably coupled to the sensor assembly. The receiving assembly is configured to selectively interact with the transmitting element to power the sensor assembly via a charging interface. A first locating feature is coupled to the support apparatus. A second locating feature is coupled to the surface assembly and configured to engage the first locating feature. The receiving assembly is aligned with the transmitting element to form the charging interface when the first locating feature is engaged with the second locating feature.

According to another aspect of the present disclosure, a charging system for a support apparatus includes a surface assembly having a surface. Transmitting elements are coupled to the surface assembly proximate to a top surface thereof. The transmitting elements are arranged in an array. A transmission unit is operably coupled to the transmitting elements. The transmission unit is configured to selectively energize the transmitting elements. A controller is communicatively coupled to the transmission unit. The controller is configured to determine the transmitting elements to be selectively energized by the transmission unit. A sensor assembly is configured to engage a person supported on the surface assembly. The sensor assembly includes a sensor for obtaining patient data. A receiving assembly is operably coupled to the sensor assembly. The receiving assembly is configured to selectively interact with at least one of the transmitting elements to power the sensor assembly.

These and other features, advantages, and objects of the present disclosure will be further understood and appreciated by those skilled in the art by reference to the following specification, claims, and appended drawings.

BRIEF DESCRIPTION OF THE DRAWINGS

In the drawings:

FIG. 21 is representative of an application interface showing an alerts view with information from a sensor assembly, according to the present disclosure;

FIG. 22 is representative of an application interface showing a push notification with an alert relating to biometrics of a patient, according to the present disclosure;

DETAILED DESCRIPTION

Figure 1:
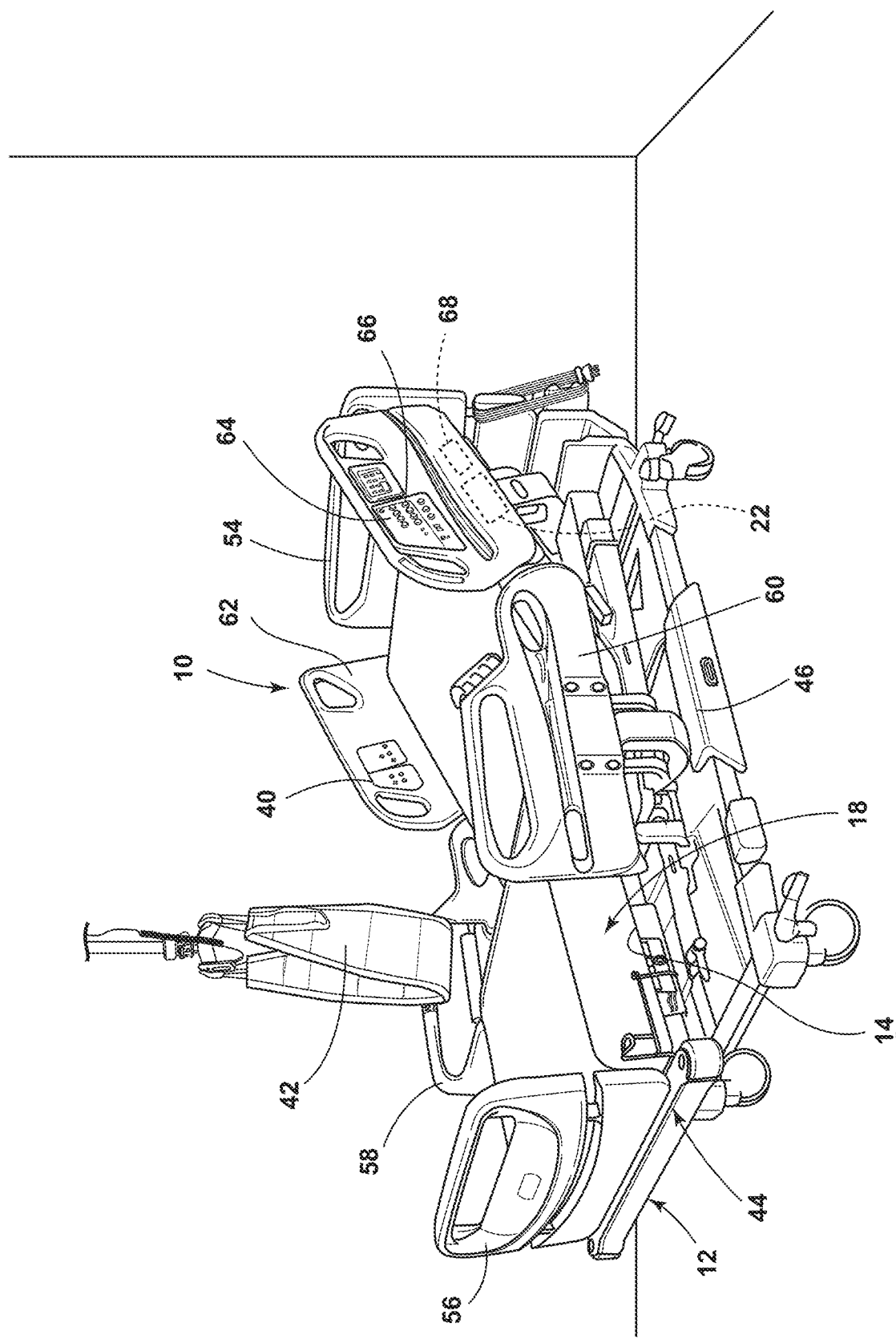
FIG. 1 is a side perspective view of a medical bed and a support sling, according to the present disclosure.

The present illustrated embodiments reside primarily in combinations of method steps and apparatus components related to a wireless power distribution embedded in a patient support surface. Accordingly, the apparatus components and method steps have been represented, where appropriate, by conventional symbols in the drawings, showing only those specific details that are pertinent to understanding the embodiments of the present disclosure so as not to obscure the disclosure with details that will be readily apparent to those of ordinary skill in the art having the benefit of the description herein. Further, like numerals in the description and drawings represent like elements.

For purposes of description herein, the terms "upper," "lower," "right," "left," "rear," "front," "vertical," "horizontal," and derivatives thereof, shall relate to the disclosure as oriented in FIG. 1. Unless stated otherwise, the term "front" shall refer to a surface closest to an intended viewer, and the term "rear" shall refer to a surface furthest from the intended viewer. However, it is to be understood that the disclosure may assume various alternative orientations, except where expressly specified to the contrary. It is also to be understood that the specific structures and processes illustrated in the attached drawings, and described in the following specification are simply exemplary embodiments of the inventive concepts defined in the appended claims. Hence, specific dimensions and other physical characteristics relating to the embodiments disclosed herein are not to be considered as limiting, unless the claims expressly state otherwise.

The terms "including," "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element preceded by "comprises a . . . " does not, without more constraints, preclude the existence of additional identical elements in the process, method, article, or apparatus that comprises the element.

Referring to FIGS. 1-26, reference numeral 10 generally designates a patient support apparatus that includes a frame 12 having a supporting surface 14. A transmitting element 16 is coupled to the frame 12. A surface assembly 18 is selectively positioned on the supporting surface 14. The surface assembly 18 includes a surface 20 for selectively enclosing an interior. A controller 22 is communicatively coupled to the transmitting element 16. A sensor assembly 24 is coupled to the surface assembly 18. The sensor assembly 24 includes a sensor 26 configured to sense information about at least one of the surface assembly 18 and a person or a patient positioned on the surface assembly 18. A receiving assembly 28 is operably coupled to the surface assembly 18 and the sensor assembly 24. The receiving assembly 28 includes a receiving element 30, which is configured to selectively interact with the transmitting element 16 via at least one of a capacitive coupling and an inductive coupling to provide power to the sensor assembly 24.

Figure 2:
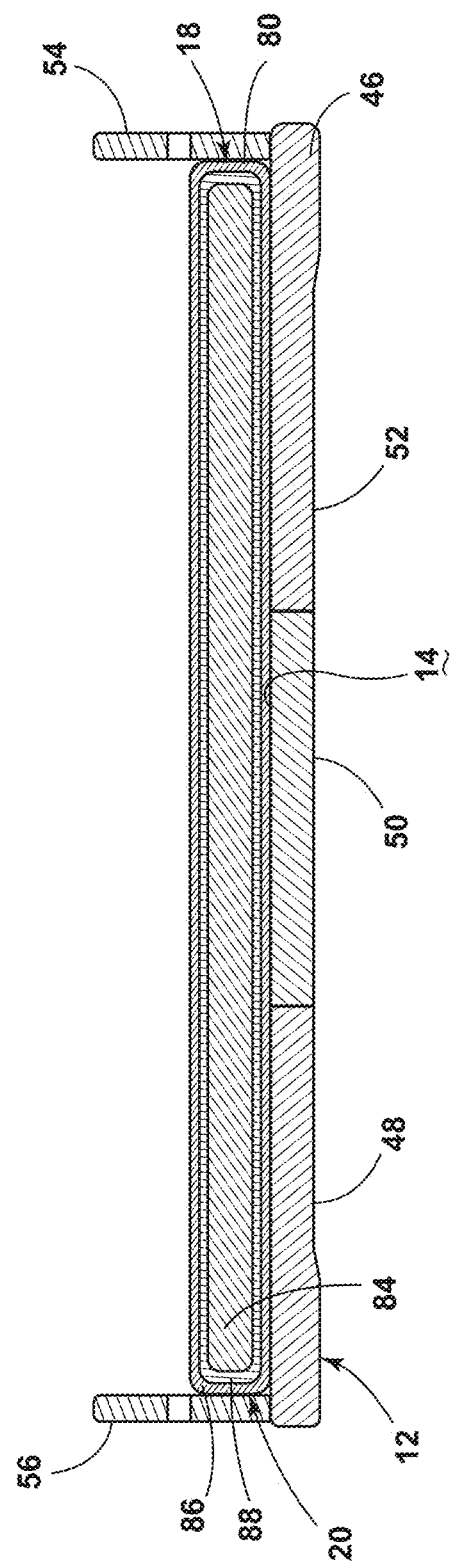
FIG. 2 is a side cross-sectional view of a surface assembly disposed on a frame, according to the present disclosure.

Referring to FIGS. 1 and 2, during a stay at a medical facility or in other healthcare settings, the patient may be positioned on or supported by the support apparatus 10. In the exemplary patient room illustrated in FIG. 1, there are two support apparatuses 10, with one support apparatus 10 configured as a medical bed 40 and the other support apparatus 10 configured as a support sling 42. It is contemplated that the support apparatus 10 may be or include the medical bed 40, a stretcher, a mattress, the surface assembly 18, a coverlet, a mattress pad, an examination table, an operating table, a recliner, the support sling 42, a lift sheet, or other suitable structures for supporting the patient.

The support apparatus 10 configured as the medical bed 40 includes an upper frame 44 and a base frame 46, that collectively form the frame 12. The upper frame 44 is generally adjustable relative to the base frame 46 (e.g., height, tilt, etc.). Additionally, the upper frame 44 includes multiple segments 48, 50, 52 that are independently movable relative to each other. The independently movable segments 48, 50, 52 allow for various portions of the upper frame 44 to be adjusted, such as, for example, an elevated head region or elevated foot region. The segments 48, 50, 52 collectively form the supporting surface 14 for supporting the surface assembly 18.

Additionally, the frame 12 includes a headboard 54 that is selectively coupled to a head end of the support apparatus 10 and a footboard 56 that is selectively coupled to a foot end of the support apparatus 10. The headboard 54 and the footboard 56 may each be fixedly coupled to the frame 12, or alternately may be removed from the support apparatus 10 to provide increased access to the patient. The support apparatus 10 includes multiple base region siderails 58, 60 and head region siderails 62, 64, which may also be considered part of the frame 12. Each of the base region siderails 58, 60 and the head region siderails 62, 64 are operable between raised and lowered positions to selectively allow access to the patient, as well as ingress and egress from the support apparatus 10.

In various examples, a user interface 66 is coupled to at least one of the siderails 58, 60, 62, 64. The user interface 66 may include buttons, a touch screen, and other selectable features that allow a caregiver or the patient to adjust aspects of the support apparatus 10, such as the position of the upper frame 44. Additionally or alternatively, the support apparatus 10 may include a position sensor 68 that senses the position of the upper frame 44. The position sensor 68 may sense the position of the upper frame 44 relative to the base frame 46, the position of the segments 48, 50, 52 of the upper frame 44, or a combination thereof.

Figure 3:
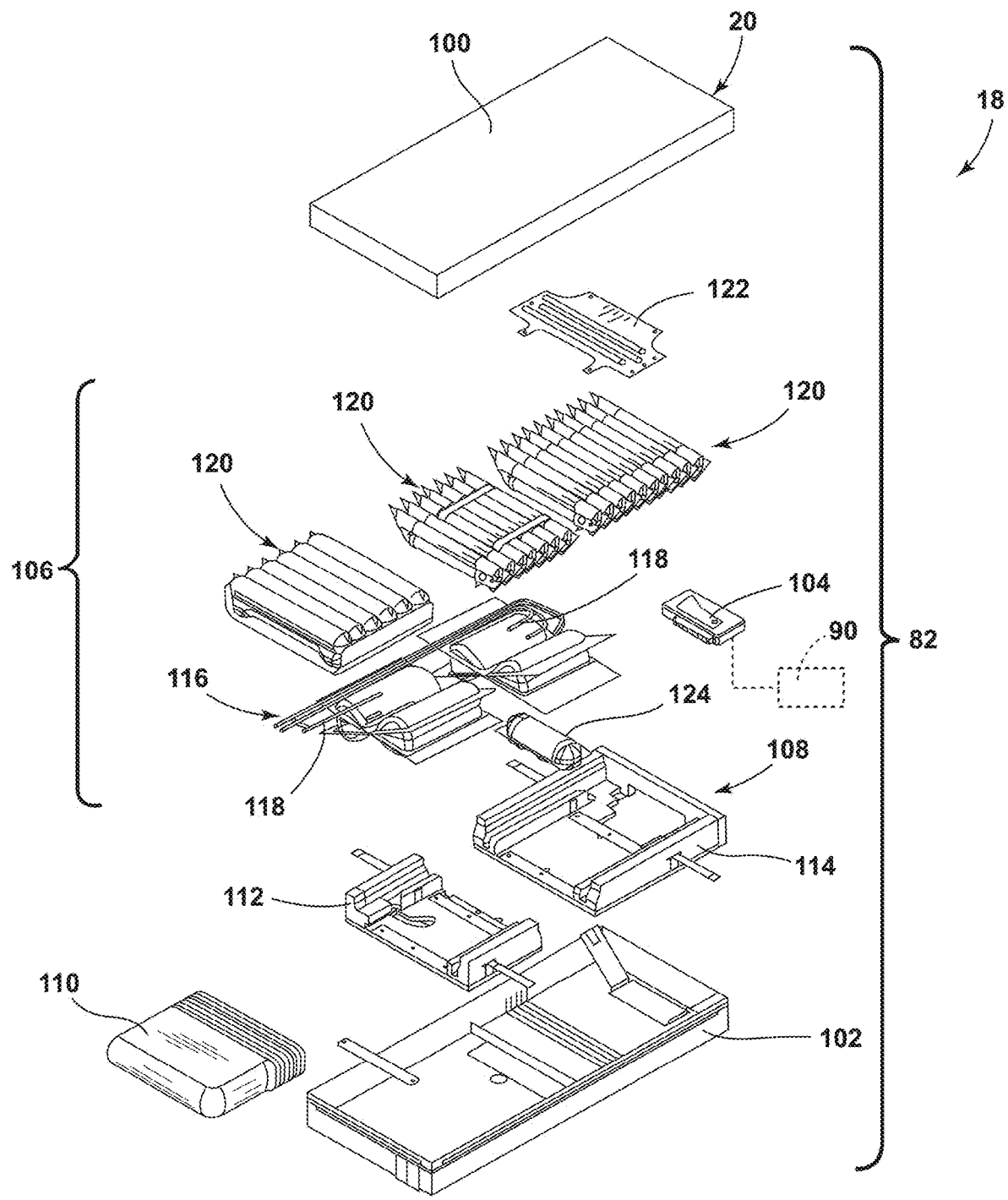
FIG. 3 is a top perspective exploded view of a surface assembly having a pneumatic system, according to the present disclosure.

Referring still to FIGS. 1 and 2 as well as FIG. 3, various components or accessories may be associated with the medical bed 40, such as, for example, the surface assembly 18. The surface assembly 18 may be a therapeutic pad, a therapeutic mattress, a therapeutic coverlet, other supports, or combinations thereof selectively positioned on the upper frame 44. The surface assembly 18 may be a non-powered surface assembly 80 or a powered surface assembly 82. In non-powered surface assembly 80 configurations, the surface assembly 18 generally includes the surface 20, which surrounds a core 84 disposed within the interior. The core 84 may be foam, springs, pads, or other suitable material that supports and provides comfort for the patient disposed on the surface assembly 18.

The surface 20 may be an outer surface, cover surface, or covering that selectively encloses the interior of the surface assembly 18. In various examples, the surface 20 includes multiple layers such as an outer or top ticking 86 and an inner or bottom ticking 88. Generally, the top ticking 86 is an outer layer that abuts the upper frame 44, and the bottom ticking 88 is disposed between the core 84 and the top ticking 86. Generally, top ticking 86 and the bottom ticking 88 are constructed of polyurethane coated nylon, or similar materials, which protect the surface assembly 18 from fluid penetration. The top ticking 86 may also have anti-skid portions to retain the surface assembly 18 in place on the support apparatus 10. The top and bottom tickings 86, 88, collectively forming the surface 20, are generally separable from the core 84 to be removed, interchanged, or replaced, which may be advantageous, for example, for cleaning. It is contemplated that the surface 20 may have additional layers without departing from the teachings herein.

Figure 12:
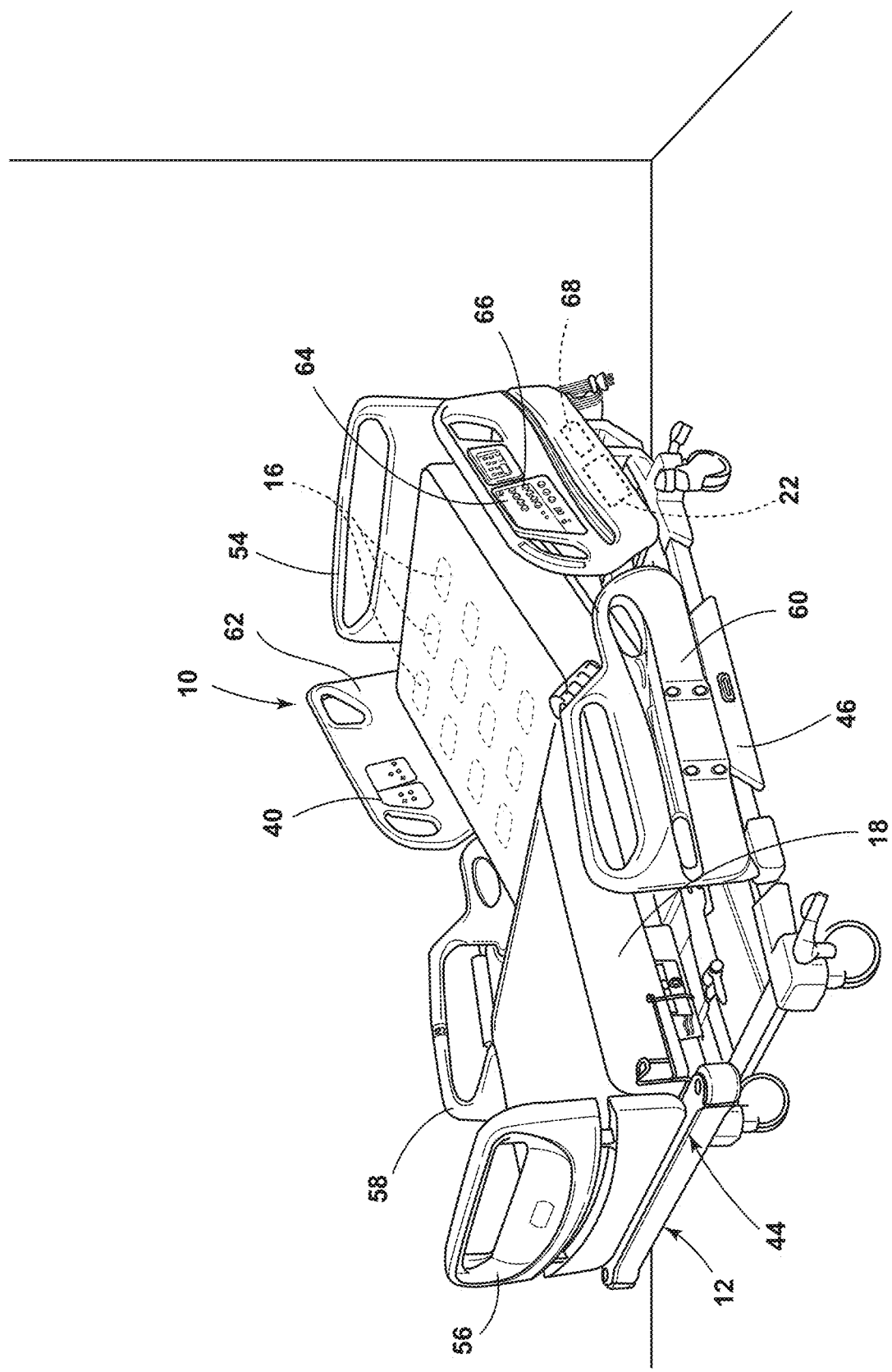
FIG. 12 is a side perspective view of a surface assembly on a medical bed where the surface assembly includes an array of transmitting elements, according to the present disclosure.

Referring still to FIG. 3, in powered surface assembly 82 configurations, the surface assembly 18 generally includes a controller 90 having a processor 92, a memory 94, and other control circuitry (FIG. 12). Instructions or routines 96 are stored in the memory 94 and executable by the processor 92. The surface assembly 18 may be communicatively coupled to the support apparatus 10 via wired or wireless communication protocols. The powered surface assembly 82 may include a pneumatic system 98 in communication with the controller 90 and enclosed within the surface 20, which may include an upper surface portion 100 and a lower surface portion 102 to allow more convenient access to the pneumatic system 98. In examples with the upper and lower surface portions 100, 102, each of the surface portions 100, 102 includes the top ticking 86 and the bottom ticking 88. Further, the upper surface portion 100 is configured to selectively couple to the lower surface portion 102 to selectively enclose and remove the surface 20 from other components of the surface assembly 82.

With reference again to FIG. 3, the pneumatic system 98 is disposed within the interior and generally includes a pump 104 in fluid communication with multiple bladders 106. The pump 104 adjusts the amount of fluid within each bladder 106 to adjust the firmness of the surface assembly 18 or provide various therapies. Each of the bladders 106 are operable between a deployed state, which is generally an inflated or expanded state, and a non-deployed state, which is generally a deflated or compressed state. The surface assembly 18 may include a shell assembly 108 that includes multiple shells 110, 112, 114 to retain the bladders 106 in selected regions of the surface assembly 18 and provide support for the pneumatic system 98. The powered surface assembly 82 may be used for pressure therapy, for example, for pressure ulcer prevention, or other treatments for the patient on the support apparatus 10.

The pneumatic system 98 may include various types of bladders 106. For example, the bladders 106 may include rotation bladders 116 for continuous lateral rotation therapy. The rotation bladders 116 may be inflated or deflated in a certain pattern to provide a gentle, side-to-side movement of the patient for prevention and treatment of pulmonary and other health complications related to immobility, as well as treat or prevent pressure ulcers. Additionally or alternatively, the rotation bladders 116 may include turn bladders 118. The turn bladders 118 are utilized to rotate the patient along a longitudinal axis based on a predefined pattern of inflation or deflation of the turn bladders 118. The turn bladders 118 may be advantageous for use in a turn assist protocol, helping the caregiver turn the patient onto his or her side to change dressings or provide other treatment.

Referring still to FIG. 3, the pneumatic system 98 may also include support bladders 120 arranged over the rotation bladders 116. The support bladders 120 may support the patient lying on the surface assembly 18. The support bladders 120 may be utilized to provide alternating pressure therapy to the patient by independently inflating, maintaining, or deflating the bladders 106 in a pattern to relieve pressure points by cyclically dropping or elevating a pressure applied by the support bladders 120. The pneumatic system 98 may also include percussion and vibration therapy (PVT) bladders 122, which may be utilized to apply percussion and vibration therapy. The PVT bladders 122 drop and elevate in pressure at a rate sufficient to impart a vibration on the patient.

Additionally or alternatively, the pneumatic system 98 may also include one or more fill bladders 124, which may be utilized to fill gaps between the support bladders 120 and the upper frame 44 as the segments 48, 50, 52 (FIG. 2) of the upper frame 44 articulate between different positions. As different segments 48, 50, 52 of the upper frame 44 move, the fill bladders 124 are inflated or deflated (i.e., adjusted between the deployed state and the non-deployed state) to fill the gap or space between adjacent segments 48, 50, 52.

Figure 4:
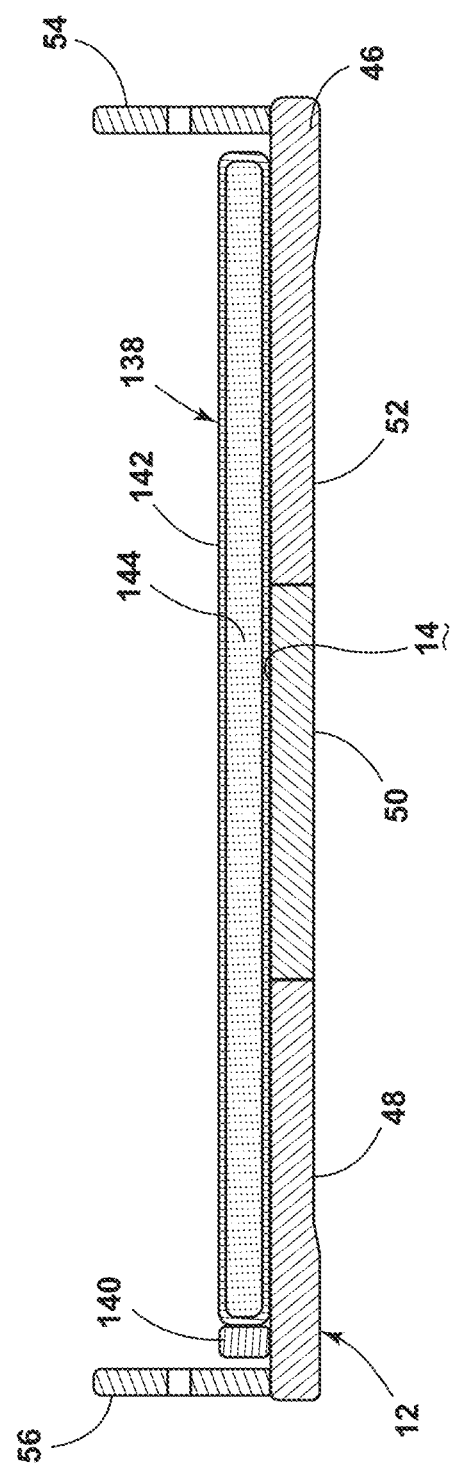
FIG. 4 is a cross-sectional view of a microclimate management system disposed on a frame of a support apparatus, according to the present disclosure.

Referring to FIG. 4, another configuration of the surface assembly 18 is or includes a microclimate management (MCM) system 138. In various examples, the MCM system 138 is selectively coupled with the support apparatus 10. The MCM system 138 generally includes a blower 140, a top coverlet 142, and a spacer material 144 within the top coverlet 142. The blower 140 operates to direct or blow air through the spacer material 144. The MCM system 138 is generally disposed on a top surface 146 of the surface assembly 18, such that the patient may rest on the MCM system 138. The MCM system 138 may also be included inside the surface assembly 18, proximate to the top surface 146 while a bottom surface 148 of the surface assembly 18 abuts the frame 12. In such examples, the MCM system 138 is configured as an MCM layer.

While the patient is positioned on the MCM system 138, air is directed through the top coverlet 142. This configuration wicks away moisture from the skin of the patient by blowing air underneath the patient, which is advantageous for preventing skin conditions that may be caused by lying on the surface assembly 18 for an extended period of time.

Figure 15:
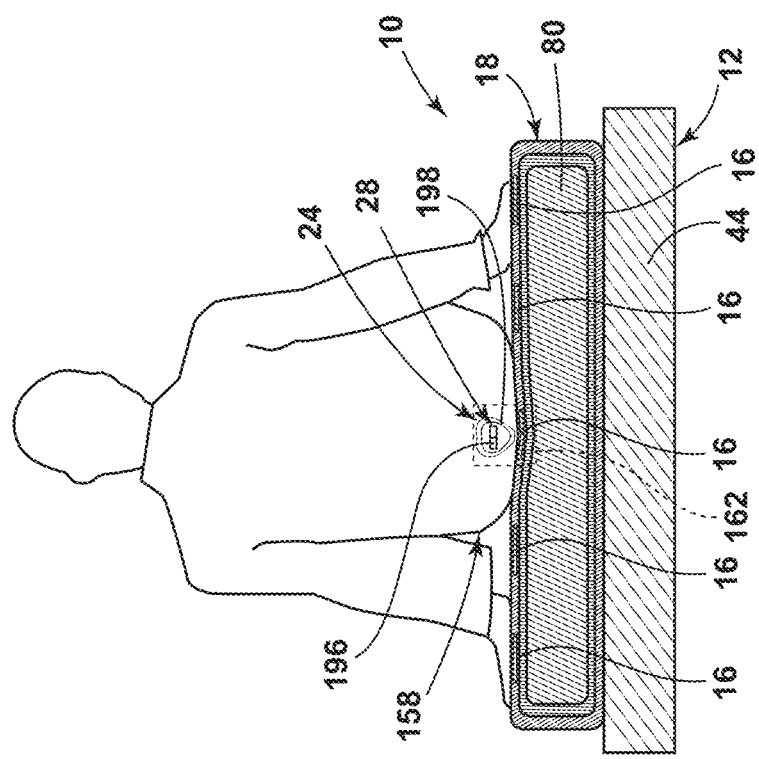
FIG. 15 is a schematic diagram of a patient wearing a sacral patch, where a sensor is coupled to the sacral patch, according to the present disclosure.

The MCM system 138 may be activated automatically when selectively coupled with the patient support apparatus 10, activated via the user interface 66 (FIG. 1) of the support apparatus 10, or activated through an application interface 150 (FIG. 15). The MCM system 138 may be used independently of or in combination with either of the non-powered surface assembly 80 and the powered surface assembly 82 configurations.

Referring to FIGS. 5-15, a charging system 158 may be utilized to wirelessly charge or power various components or accessories associated with the support apparatus 10, including the surface assembly 18, the sensor assembly 24, and the MCM system 138. Additionally, the charging system 158 may be utilized to power the sensor assembly 24 when the sensor assembly 24 is coupled to the patient. The charging system 158 may provide some or all of the electrical power for these components associated with the support apparatus 10 and the patient. The charging system 158 is advantageous for providing electrical power through a mechanical barrier.

The charging system 158 generally includes the transmitting element 16 coupled with the support apparatus 10 and/or the surface assembly 18 and the separable receiving assembly 28 that includes the receiving element 30 and a storage feature 160. The receiving assembly 28 may be coupled with, for example, the surface assembly 18 and/or the MCM system 138, thereby reducing or eliminating direct mechanical connections between these components and the support apparatus 10. Further, the charging system 158 may reduce connections between the patient and the support apparatus 10 or the surface assembly 18. A charging interface 162 is defined between the transmitting element 16 and the receiving assembly 28 to wirelessly transmit energy or power from the transmitting element 16 to the receiving element 30. The power transfer is electromagnetic, utilizing capacitive coupling, inductive coupling, or both.

The receiving assembly 28 generally includes a control unit 168 that has a processor 170, a memory 172, and other control circuitry. Instructions or routines 174 are stored in the memory 172 and executable by the processor 170. The control circuitry may include communication circuitry 176 for wireless communication. At least one routine 174 may be directed to collecting energy from the charging interface 162 and converting the energy for storage in the storage feature 160.

The charging system 158 is utilized to transfer power from the support apparatus 10 or surface assembly 18 to the accessory, component, or sensor 26 operably coupled with the receiving assembly 28. The transmitting element 16 may be coupled to a surface of the support apparatus 10, as illustrated in FIGS. 5-10, and/or the surface assembly 18, as illustrated in FIGS. 11-15. In certain aspects, the transmitting element 16 may be embedded within the support apparatus 10 or otherwise received within a recess of the support apparatus 10 to provide a smooth surface, reducing the pressure that may be applied to the patient through the surface assembly 18.

In examples where the transmitting element 16 is coupled to the support apparatus 10, the transmitting element 16 may be coupled to the upper frame 44 (see FIG. 6), such as on the supporting surface 14, a periphery of the frame 12, such as on one or more of the siderails 58, 60, 62, 64 (see FIG. 7) and/or the footboard 56 (see FIG. 10), another practicable location on the support apparatus 10, or combinations thereof. In examples where the transmitting element 16 is coupled to the surface assembly 18, the transmitting element 16 may be coupled to or embedded in the surface 20 (see FIG. 13) or another practicable location on the surface assembly 18.

The transmitting element 16 and the receiving element 30 may each be positioned to maximize the power transfer via the charging interface 162. Additionally or alternatively, the transmitting element 16 and the receiving element 30 may be positioned to form a strong coupling coefficient between the transmitting element 16 and the receiving element 30. The coupling coefficient is generally a strength of the interaction between the receiving element 30 and the transmitting element 16. A stronger coupling coefficient generally provides more efficient charging. Further, the charging system 15 may include any practicable number of transmitting elements 16 and receiving elements 30 to provide power to various components, accessories, sensors 26, etc.

Referring still to FIGS. 5-15, the transmitting element 16 and the receiving element 30 selectively interact via the charging interface 162, which includes at least one of inductive coupling and capacitive coupling, to transfer power. The transmitting element 16 is a source configured to transfer power from a power source 178 to the receiving element 30 of the receiving assembly 28. The power source 178 is generally a power supply of the medical facility, but may also be a battery or rechargeable battery of the support apparatus 10. The transfer of power from the power source 178 to the receiving element 30 may charge (e.g., increases a state of charge) of the receiving assembly 28.

In inductive coupling examples, the transmitting element 16 and the receiving element 30 are generally configured as coils. An alternating current is generated through the transmitting element 16 to create an oscillating magnetic or electromagnetic field between the transmitting element 16 and the receiving element 30 in the charging interface 162. The electromagnetic field passes through the receiving element 30 to induce an alternating voltage. The receiving assembly 28 includes circuitry to capture or extract power from the electromagnetic field and convert the energy into electricity. The receiving assembly 28 also includes circuitry for directing and controlling the power supply to the storage feature 160.

In capacitive coupling examples, the transmitting element 16 and the receiving element 30 are generally configured as electrodes. An alternating voltage is applied to the transmitting element 16 by the power source 178 to generate an oscillating electric field. The electric field generally induces an alternating potential on the transmitting element 16. Capacitance is used for the transfer of power between the transmitting element 16 and the receiving element 30, with the space between the transmitting and receiving elements 16, 30 serving as a dielectric. The receiving assembly 28 includes circuitry to capture or extract power from the electric field and convert the energy into electricity. The receiving assembly 28 also includes circuitry for directing and controlling the power supplied to the storage feature 160. It is contemplated that other forms of wireless power transmission may be employed in the charging system 158 such as, for example, magnetic resonance, loose coupled resonance, electromagnetic radiation without departing the teachings herein.

Referring still to FIGS. 5-15, when the receiving element 30 is positioned within a predefined distance from the transmitting element 16, the charging interface 162 is formed to wirelessly transmit power from the transmitting element 16 to the receiving element 30. Generally, for greater energy transfer, the predefined distance is less than or equal to about 5 mm. For lesser energy transfer, the predefined distance may be less than or equal to about 10 cm. The receiving element 30 collects energy from the charging interface 162, converts the energy, and transfers the energy to the storage feature 160, which generally provides power separate from the active power transfer.

The alignment between the receiving element 30 and the transmitting element 16 affects the efficiency of the power transfer to the receiving assembly 28. When the transmitting element 16 is coupled to the support apparatus 10, the support apparatus 10 and the corresponding component (i.e., the component having the receiving element 30) may have complementary locating features 164, 166 to assist in this alignment. For example, the surface assembly 18 or the MCM system 138 may include the first locating feature 164, which mates with the second locating feature 166 on the support apparatus 10 to bring the electrical power aspects (i.e., the receiving element 30 and the transmitting element 16) into alignment. The locating features 164, 166 are generally flush with a surrounding surface. Further, the locating features 164, 166 may be magnetic, pneumatic, or any other practicable configuration.

Further, the complementary locating features 164, 166 may provide a holding force to maintain the alignment between the receiving element 30 and the transmitting element 16. In various aspects, the locating features 164, 166 may be mating magnets. In additional or alternative examples, the locating feature 164 may be a magnet and the second locating feature 166 may be a plate or component with magnetic properties or vice versa. The locating features 164, 166 may assist in providing initial alignment to form the charging interface 162 and retain the alignment for continual power transfer.

The locating features 164, 166 are generally magnetic and flush with a surrounding surface (e.g., the supporting surface 14, the surface 20 of the surface assembly 18, etc.). In such examples, the first locating feature 164 is a first magnet flush with the surface 20 of the surface assembly 18, and the second locating feature 166 is a second magnet flush with the supporting surface 14 and configured to magnetically engage the first magnet. The flush configuration of the magnetic locating features 164, 166 may be advantageous for efficient cleaning and positioning of the surface assembly 18, as well as for reducing collection of "bioburden" or biological materials.

The location of the locating features 164, 166 may depend on the location of the transmitting element 16 and the receiving element 30. For example, the locating features 164, 166 may be located proximate to the transmitting element 16 and the receiving element 30 to provide sufficient alignment without interfering with the charging interface 162. The locating features 164, 166 may also be used when the transmitting element 16 is coupled to the surface assembly 18 without departing from the teachings herein.

Referring still to FIGS. 5-15, the storage feature 160 of the receiving assembly 28 is generally smaller than a battery. In various examples, the storage feature 160 is a supercapacitor. The small size of the storage feature 160 is advantageous for reducing interface pressure on the patient and not substantially disrupting an airflow path within the MCM system 138. An energy or charge level with the storage feature 160 may be continually refreshed by the power transferred through the charging interface 162 (e.g., the active power transfer). Additionally or alternatively, the charge level may be intermittently refreshed based on a threshold condition, for example when the charge level is below a predefined charge level, the component being powered is active, etc.

The storage feature 160 allows ratcheting up of available energy, as power can be transferred on time-varying electromagnetic conditions. Depending on what component or accessory the receiving assembly 28 is powering, the component being charged may operate in a low energy state with intermittent high energy states. The low energy state may be a default condition, such as a standby or sleep mode, whereas the high energy state may be an active state, a state allowing for data transfer, etc. The storage feature 160 may provide energy for the different operating states.

Referring still to FIG. 5-15, the receiving assembly 28 powers various configurations of the sensor assembly 24, which utilizes the sensor 26 to sense information relevant to the care and treatment of the patient. The sensor assembly 24 is generally configured to be powered by the receiving assembly 28 and communicate data wirelessly through a wireless data transfer, as described further herein. The sensor assembly 24 may be configured to operate in a low energy state when off or when sensing data and a high energy state when wirelessly transferring data. The wireless sensor assembly 24 provides increased flexibility to the caregiver in obtaining data about the patient (e.g., patient data), as well as minimizes wires and other features that may contribute to discomfort or the development of a pressure injury on the patient. The wireless sensor assembly 24 may also increase the accuracy of sensed information.

The sensor assembly 24 is powered through communication with the receiving assembly 28. The amount of power that is transferred to the receiving element 30 to power the sensor assembly 24 may be small enough that poor coupling between the receiving element 30 and the transmitting element 16 may be tolerated. Poor coupling may be caused by, for example, greater distance between the receiving element 30 and the transmitting element 16 or patient movement.

While positioned on the support apparatus 10, a variety of information may be obtained about the patient and the surface assembly 18 via the sensor assembly 24. The sensor assembly 24 may be coupled to the surface assembly 18 (see FIGS. 5-10), to the patient (see FIGS. 11-15), to the MCM system 138, or combinations thereof. The sensor assembly 24 may include a single sensor 26 or multiple sensors 26. In configurations with multiple sensors 26, each sensor 26 may be configured to detect the same information, or alternatively, the sensors 26 may be configured to detect combinations of different information. In non-limiting examples, the sensor assembly 24 coupled to the surface assembly 18 may include at least one of a biometric sensor 180, a bladder pressure sensor 182, an identification sensor 184, a humidity sensor 186, a temperature sensor 188, and an airflow sensor 190, which may collectively be referred to herein as the sensors 26. Additional sensors 26 may be associated with the surface assembly 18 and/or the MCM system 138 to sense different or additional information without departing from the teachings herein.

Figure 6:
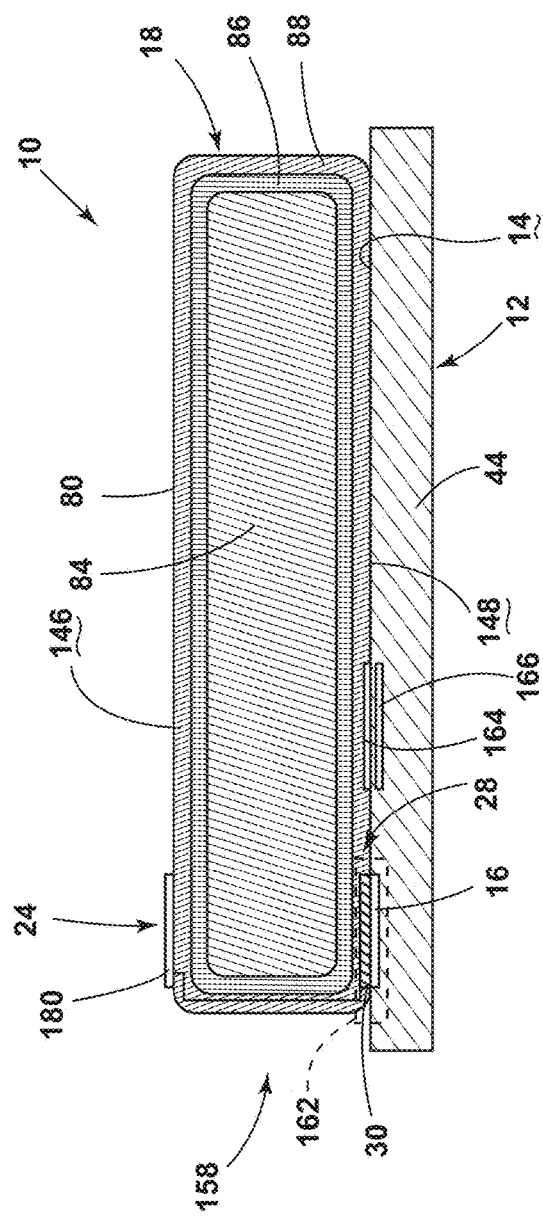
FIG. 6 is a cross-sectional view of a surface assembly having a sensor assembly operably coupled to a receiving assembly, where the receiving assembly interacts with a transmitting element on a supporting surface of a support apparatus, according to the present disclosure.
Figure 7:
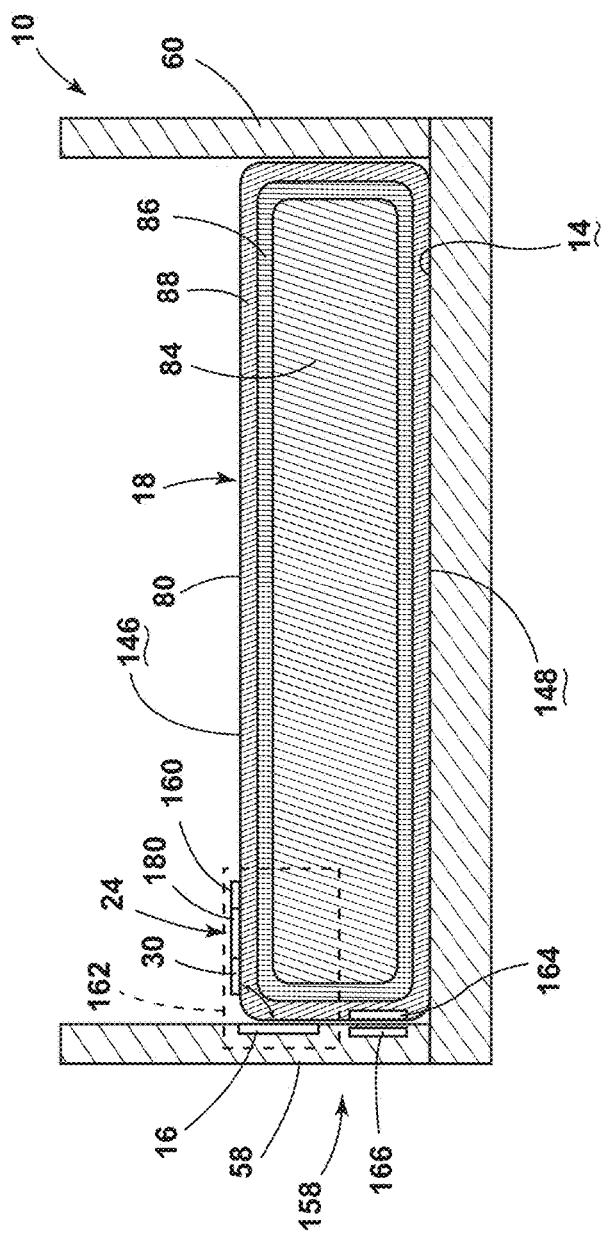
FIG. 7 is a cross-sectional view of a surface assembly having a sensor assembly operably coupled to a receiving assembly, where the receiving assembly interacts with a transmitting element on a siderail of a support apparatus, according to the present disclosure.

Referring still to FIGS. 6 and 7, in the illustrated example, the sensor assembly 24 includes the biometric sensor 180 coupled to the top ticking 86 of the surface assembly 18. In certain aspects, the biometric sensor 180 may be printed onto the top ticking 86. In such examples, the biometric sensor 180 may be a thin layer on the top ticking 86 or flush with the top ticking 86 to minimize the pressure applied to the patient. The biometric sensor 180 is powered by the receiving assembly 28. The biometric sensor 180 is configured to obtain biometric data from the patient. The biometric data may include, for example, heart rate, respiration rate, glucose, blood pressure, skin conductivity, blood surface, saturation O₂, respiration rate, thoracic sounds, and other physiological attributes of the patient. The biometric data may be wirelessly communicated to the controller 22 of the support apparatus 10, as discussed further herein.

In the illustrated example of FIG. 6, the biometric sensor 180 is coupled to the surface 20 of the surface assembly 18 and configured to engage the patient (e.g., on an outer side of the surface 20). In the illustrated configuration, the biometric sensor 180 is coupled to the top surface 146 of the top ticking 86 that engages the patient. The biometric sensor 180 being coupled to the top surface 146 of the top ticking 86, or otherwise on the outer top side of the surface 20, allows the biometric sensor 180 to be in closer proximity to, engage, or in contact with the patient on the surface assembly 18 to obtain the biometric data. The receiving assembly 28 is coupled to the bottom surface 148 of the top ticking 86, or otherwise on an outer bottom side of the surface 20, to be within the predefined distance of the transmitting element 16 coupled to the supporting surface 14 of the upper frame 44. The biometric sensor 180 is operably coupled with the receiving assembly 28, which may generally be via wiring extending through the top ticking 86 or between the top ticking 86 and the bottom ticking 88. The wiring extending through the surface 20 isolates the wires in the surface 20 of the surface assembly 18, allowing the surface 20 to be removed more conveniently. When the surface assembly 18 is positioned on the upper frame 44, the receiving element 30 is aligned with the transmitting element 16, the charging interface 162 is formed, and the biometric sensor 180 is powered.

It is also contemplated that the biometric sensor 180 may be coupled to the coverlet 142 of the MCM system 138 without departing from the teachings herein. In such examples, the transmitting element 16 may be positioned elsewhere on the frame 12, such as one of the siderails 58, 60, 62, 64, or on the surface assembly 18 to reduce the distance between the transmitting element 16 and the receiving element 30 as described herein. Alternatively, the MCM system 138 configured as the MCM layer may be in communication with the receiving assembly 28 coupled to the top ticking 86.

In the illustrated example of FIG. 7, the transmitting element 16 is coupled to an inner surface of the side rail 58. When the transmitting element 16 is coupled to the siderail 58, the receiving element 30 may be coupled to the top surface 146 of the top ticking 86 proximate to the biometric sensor 180. This configuration may reduce wiring extending through surface 20. The transmitting element 16 on the siderail 58 is configured to align (e.g., be within sufficient distance) with the receiving assembly 28 to form the charging interface 162. In various aspects, the transmitting element 16 may align with the receiving assembly 28 when the siderail 58 is in the raised position. In this configuration, the first locating feature 164 may be coupled to a side of the surface assembly 18, while the second locating feature 166 is coupled to the inner surface of the siderail 58. The positioning of the locating features 164, 166 may assist with aligning the receiving element 30 with the transmitting element 16, as well as maintaining the alignment therebetween.

It is also contemplated that the transmitting element 16 on the siderail 58 may be configured to align with the receiving assembly 28 when the siderail 58 is in the lowered position. In such examples, the receiving assembly 28 may be disposed on the top surface 146, the bottom surface 148, and/or a side of the surface 20 of the surface assembly 18. Further, the transmitting element 16 may be configured to align with different receiving assemblies 28 when in the raised and lowered positions. In such examples, one receiving assembly 28 may be coupled to the top surface 146 while a second receiving assembly 28 is coupled to the bottom surface 148.

The positioning of the biometric sensor 180, the transmitting element 16, and the receiving assembly 28 are merely exemplary and not meant to be limiting. The receiving assembly 28 may be positioned in any practicable location that forms the charging interface 162 with the transmitting element 16. Depending on the configuration of the charging system 158 and the component to be powered, the transmitting element 16 may be coupled to the supporting surface 14, the headboard 54, the footboard 56, at least one of the siderails 58, 60, 62, 64, or combinations thereof.

Referring again to FIGS. 8 and 9, the sensor assembly 24 may include the bladder pressure sensors 182 configured to detect pressure data from within the bladders 106 of the pneumatic system 98. The bladder pressure sensors 182 may be coupled to or disposed within the bladders 106 to obtain the pressure data. The transmitting element 16 is illustrated as a single element associated with each bladder 106, extending across the supporting surface 14. It is contemplated that multiple transmitting elements 16 may be included without departing from the teachings herein.

Figure 8:
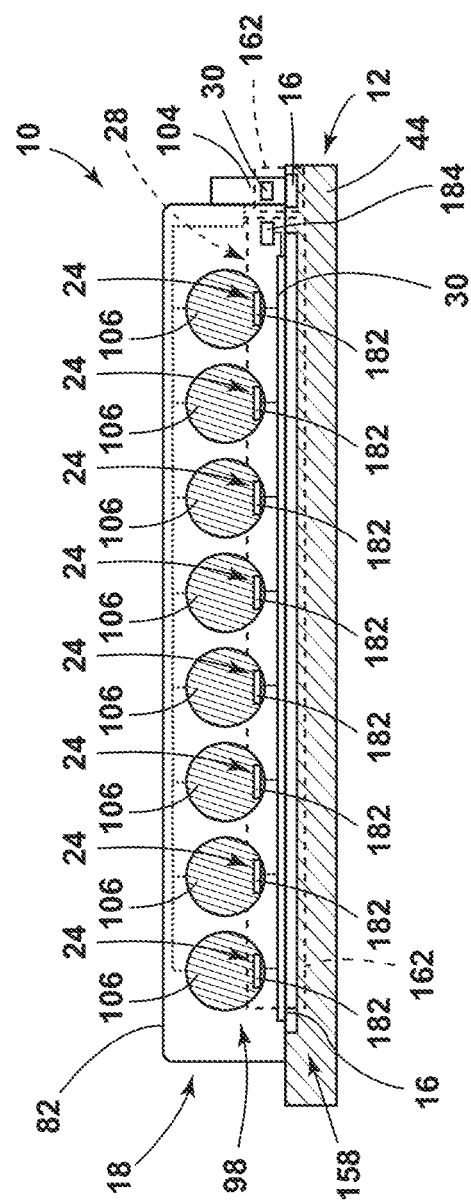
FIG. 8 is a cross-sectional view of a surface assembly having a pneumatic system, where the pneumatic system includes a pump and is associated with sensors that are each operably coupled with a receiving assembly, according to the present disclosure.

In the illustrated example of FIG. 8, a single receiving element 30 is disposed proximate to a bottom of the surface assembly 18. The receiving element 30 may power some or all of the bladder pressure sensors 182. In such examples, wiring may extend from the receiving element 30 to each bladder pressure sensor 182.

Figure 9:
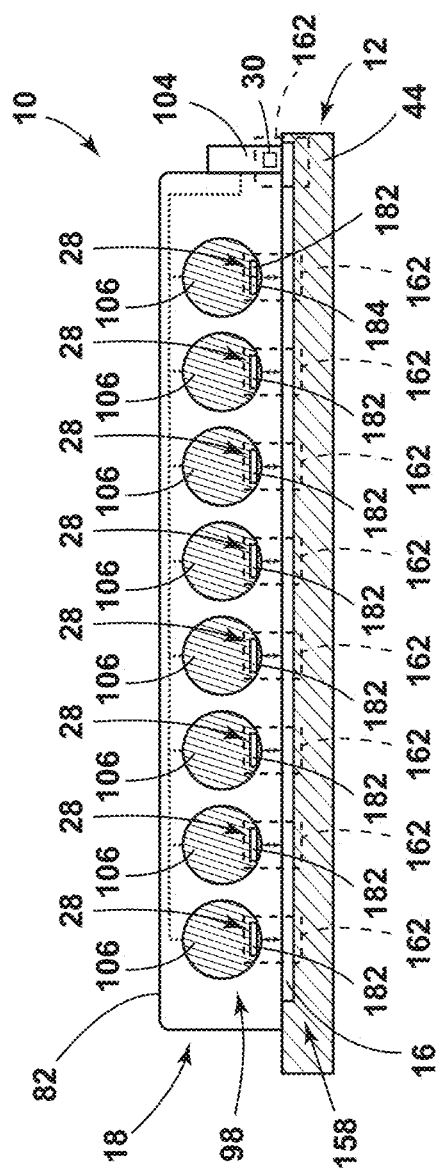
FIG. 9 is a side cross-sectional view of a surface assembly having a pneumatic system, where the pneumatic system includes a pump and is associated with sensors that are each operably coupled with corresponding receiving assemblies, according to the present disclosure.
Figure 10:
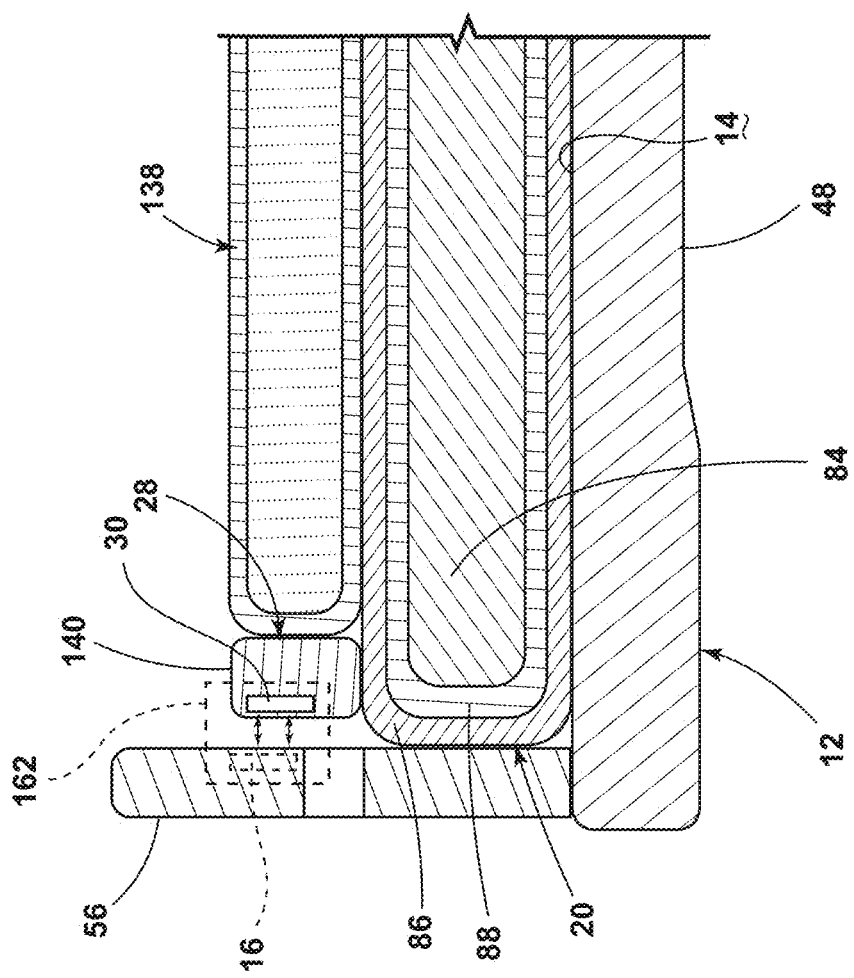
FIG. 10 is a partial cross-sectional view of a microclimate management system having a blower operably coupled with a receiving assembly that interacts with a transmitting element coupled to a support apparatus, according to the present disclosure.

In the example illustrated in FIG. 9, each bladder 106 may include the receiving assembly 28 associated with the corresponding bladder pressure sensor 182. In such examples, wiring for powering the bladder pressure sensors 182 may be reduced compared to the example illustrated in FIG. 8. Each bladder pressure sensor 182 may be powered by a corresponding receiving assembly 28 that selectively interacts with the transmitting element 16.

Referring still to FIGS. 8 and 9, each bladder pressure sensor 182 is configured to transmit data wirelessly, as described further herein. Use of the wireless sensor assemblies 24 reduces sense line tubes within the surface assembly 18, offering more space for other features. Further, reducing or removing sense lines within the surface assembly 18 reduces the possibility of a kinked sense line, which could measure the wrong pressure. Therefore, utilizing wireless sensor assemblies 24 with the pneumatic system 98 may provide increased accuracy in sensing the pressure data.

As illustrated in FIGS. 8 and 9, the charging system 158 may also be utilized to power other electronic components of the powered surface assembly 82, such as the pump 104. The pump 104 may be in communication with the receiving assembly 28 associated with the bladders 106, or alternatively may include a separate receiving assembly 28 with a separate receiving element 30 and storage feature 160. The receiving assembly 28 selectively interacts with the transmitting element 16 to provide power to the pump 104, allowing the pump 104 to be activated and adjust the bladders 106 of the pneumatic system 98. The pump 104 may operate in a lower energy state when off or idle and a high energy state when adjusting the fluid in the bladders 106. The size and number of transmitting elements 16 in the charging system 158 may depend on the location, size, and number of components to be powered.

Additionally or alternatively, the sensor assembly 24 may also include an identification sensor 184 (e.g., one of the sensors 26) that senses or otherwise stores information about the surface assembly 18, such as a type of surface assembly 18. For example, the identification sensor 184 exemplified in FIGS. 6 and 7 may sense that the surface assembly 18 is the non-powered surface assembly 80. In the example in FIGS. 8 and 9, the identification sensor 184 may sense that the surface assembly 18 is the powered surface assembly 82 having the pneumatic system 98.

The identification data may affect the function of the support apparatus 10, the charging system 158, or a combination thereof. In certain aspects, the type of component to be powered may determine how much power is transferred through the charging interface 162. For example, when the sensor assembly 24 is coupled to the non-powered surface assembly 80, power is transferred to power the sensor assembly 24. In another example, when the powered surface assembly 82 is utilized, the charging system 158 transfers power for the sensor assembly 24 and the pump 104. Powering the pump 104 generally utilizes a greater amount of power from the charging system 158 compared to the sensor assembly 24.

Additional sensors 26 may be included in the sensor assembly 24 within or coupled to the surface assembly 18 and/or the MCM system 138. For example, the sensor 26 may be configured as the humidity sensor 186 to sense humidity within or proximate to the surface assembly 18 and/or the MCM system 138. In another non-limiting example, the sensor 26 may be configured as the temperature sensor 188 to sense temperature data within or proximate to the surface assembly 18 and/or the MCM system 138. Further, the sensor 26 may be the airflow sensor 190, which is configured to sense airflow (e.g., speed, strength, etc.) through the MCM system 138. The airflow sensor 190 may also be configured to sense a speed of the blower 140. In certain aspects, the MCM system 138 may include the humidity sensor 186 and the temperature sensor 188 to sense humidity and temperature of the airflow through the MCM system 138. This may be advantageous as the airflow is utilized for cooling and wicking moisture from the patient and can be utilized to monitor heat and moisture being directed away from the patient.

Other configurations of sensors 26 may be utilized to provide surface information, which may be advantageous for controlling functions of the surface assembly 18, with or without the MCM system 138 included. For example, the sensors 26 may be immersion sensors for sensing a depth the patient is positioned in the surface assembly 18 (e.g., how far into the surface assembly 18 the patient sinks). The immersion sensors 26 may be configured as capacitive sensors. Additionally or alternatively, the sensor 26 may be configured as or include a blower speed sensor, for monitoring the function of the blower 140 of the MCM system 138.

The surface information may include at least one of, but not limited to, MCM airflow, MCM temperature, MCM humidity, MCM blower speed, bladder pressure, patient immersion, a type of surface assembly, or any combinations thereof. The sensors 26 may sense any practicable surface information, which is advantageous for determining and controlling the performance and/or functionality of the surface assembly 18. The sensors 26 may be configured to obtain any practicable data helpful for caring for the patient, as well as for controlling the surface assembly 18.

Referring again to FIG. 10, the charging system 158 may also be utilized to power the blower 140 of the MCM system 138. The blower 140 may be coupled with the receiving assembly 28 to receive power similar to the pump 104 of the pneumatic system 98. In the illustrated configuration, the receiving assembly 28 for the blower 140 is separate from the receiving assembly 28 or receiving assemblies 28 for powering components of the surface assembly 18. Further, the identification sensor 184 may be configured to sense when the MCM system 138 is utilized rather than the pneumatic system 98. The blower 140 associated with the MCM system 138 is generally smaller than the pump 104 associated with the pneumatic system 98, thereby utilizing less power. The charging system 158 may then transfer less power when the blower 140 is being powered compared to when the pump 104 is being powered.

The sensor assembly 24 may also be disposed in or otherwise coupled to the MCM system 138. For example, the sensor 26 may be configured to sense temperature and/or humidity of airflow within the MCM system 138. In another example, the sensor 26 may be the airflow sensor 190 configured to sense the strength of the airflow through the MCM system 138. Additionally or alternatively, the sensor 26 may be configured to sense air pressure within the MCM system 138.

The information sensed from the MCM system 138 (e.g., the surface information) may be utilized to intermittently activate and control the MCM system 138. For example, the sensed temperature and humidity may indicate that the MCM system 138 may be deactivated. The intermittent activation and control of the MCM system 138 may provide increased control of the MCM system 138, which may be advantageous for saving energy. Saving energy may save battery power or reduce electromagnetic waves from decreased use of the charging interface 162. The sensor 26 may be configured to sense any practicable information helpful for caring for the patient.

Referring again to FIG. 11, the sensor assembly 24 may be coupled to the patient or be worn by the patient to obtain the patient data (e.g., biometric data, position of the patient, pressure related to pressure injury development, etc.). The sensor 26 may be in contact with, engage, or disposed in close proximity to the patient to obtain the sensed data. The sensor assembly 24 is in communication with the receiving assembly 28 to receive power from the charging interface 162 and the storage feature 160. In certain aspects, the sensor assembly 24 and the receiving assembly 28 are a single unit to minimize wiring when worn by the patient. In the illustrated configuration, the transmitting element 16 is coupled to the surface assembly 18 to form the charging interface 162 between the transmitting element 16 and the receiving assembly 28. The transmitting element 16 may, additionally or alternatively, be coupled to one of the siderails 58, 60, 62, 64 or on other surfaces of the support apparatus 10 proximate to the patient.

Figure 11:
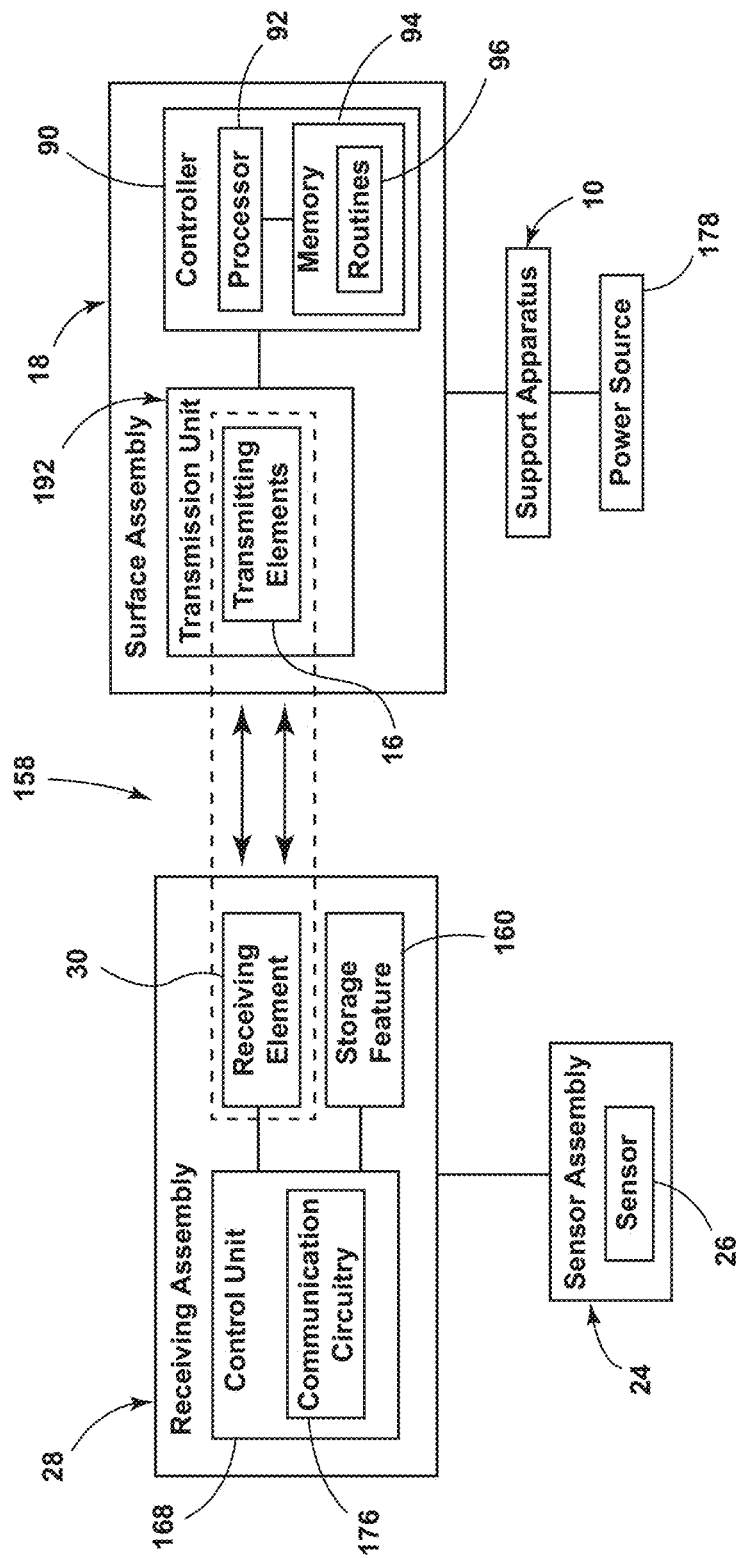
FIG. 11 is a block diagram of a charging system with a transmitting element coupled to a surface assembly, according to the present disclosure.

Referring still to FIG. 11, as well as FIG. 12, the surface assembly 18 may include multiple transmitting elements 16 arranged in an array along a portion, or an entirety of, the top surface 146 of the surface assembly 18. Alternatively, a single transmitting element 16 may extend across a substantial portion or the entirety of the top surface 146. In examples with multiple transmitting elements 16, a transmission unit 192 may be utilized to selectively energize the transmitting elements 16. The transmission unit 192 may be communicatively coupled with each transmitting element 16 and at least one of the controller 90 of the surface assembly 18 and the controller 22 of the support apparatus 10. The transmission unit 192 may receive control signals related to which transmitting elements 16 to activate. The transmission unit 192 may direct or guide power from the power source 178 to the select transmitting elements 16. Depending on the configuration of the sensor 26 to be powered and/or the location of the sensor 26, different transmitting elements 16 may be energized to emit fewer electromagnetic waves. The charging system 158 may energize the transmitting elements 16 that most efficiently power the sensor 26 based on the type of sensor 26 and the position of the sensor 26.

The transmitting elements 16 being selectively energized reduces the electromagnetic fields generated proximate to the patient. Moreover, charging the sensor 26 may be performed at a lower energy level compared to charging the pump 104 or the blower 140. Each component to be powered may be powered separately, in combination, or in various combinations. For example, the least amount of energy may be transferred when powering the sensor 26 separate from the pump 104 and the blower 140. Use of lower energy levels and selectively energized transmitting elements 16 may be advantageous for reducing or preventing interference with implanted devices of the patient (e.g., a defibrillator, etc.).

In the illustrated configuration, the surface assembly 18 is electrically coupled to the support apparatus 10, allowing energy from the power source 178 to be provided to the surface assembly 18 through the support apparatus 10. The power supplied from the power source 178 powers the transmitting elements 16 in the surface assembly 18. It is contemplated that the surface assembly 18 and/or the MCM system 138 may be standalone units configured to directly engage the power source 178 without departing from the teachings herein.

Figure 13:
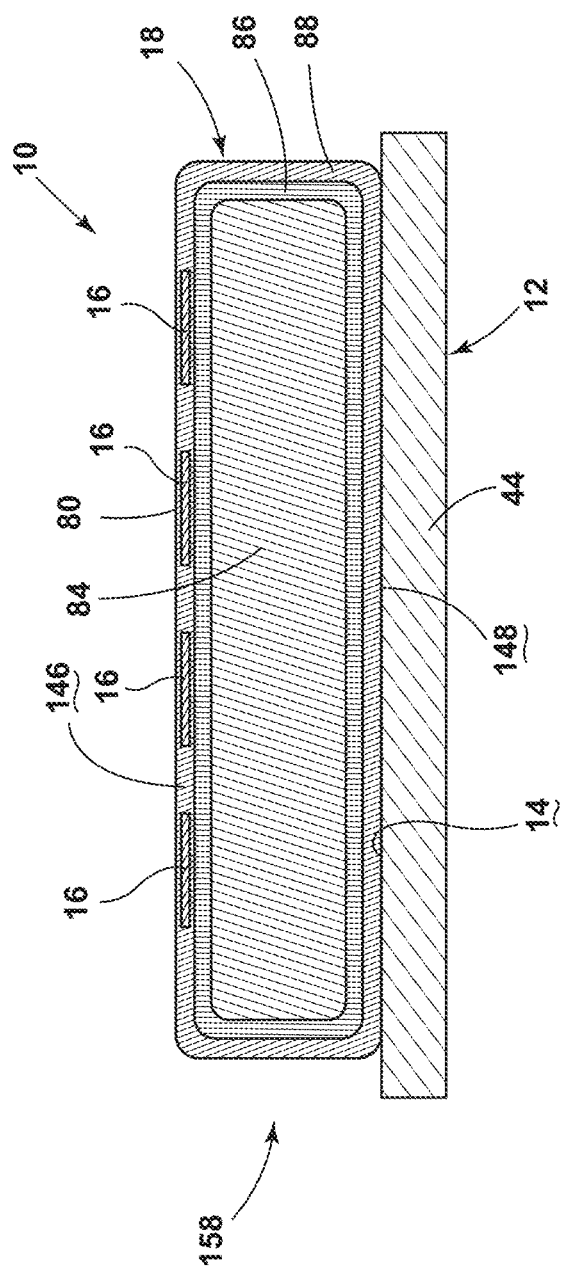
FIG. 13 is a cross-sectional view of a surface assembly having an array of transmitting elements, according to the present disclosure.
Figure 14:
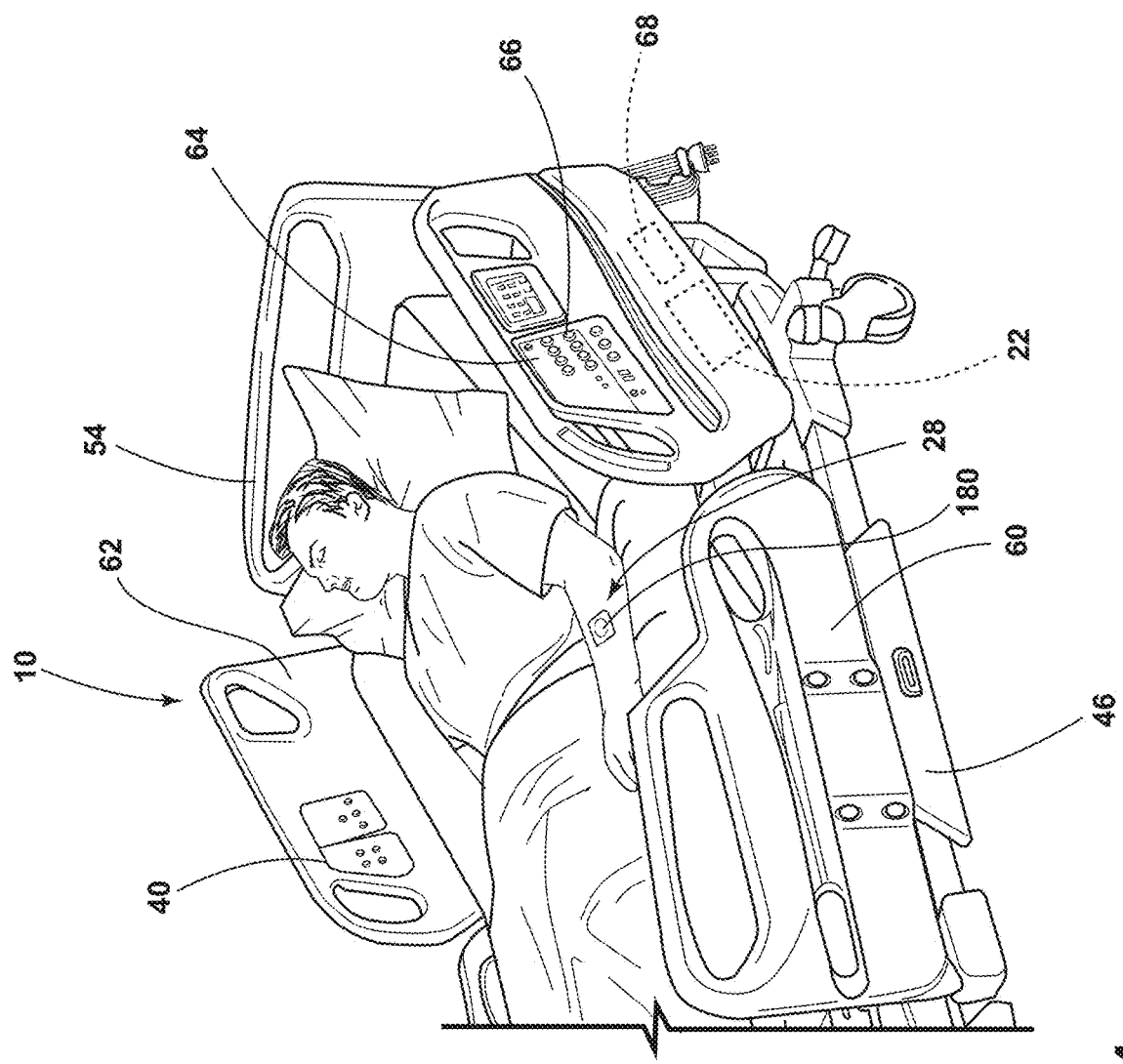
FIG. 14 is a side perspective view of a patient disposed on a support apparatus where the patient is wearing a biometric sensor that is charged by a charging system, according to the present disclosure.

Referring still to FIG. 12, as well as to FIG. 13, the transmitting elements 16 are arranged on or proximate to the top surface 146 of the surface assembly 18. The transmitting elements 16 may define an array or matrix, having x-number of transmitting elements 16 arranged laterally across the surface assembly 18 and y-number of transmitting elements 16 arranged in a longitudinal direction across the surface assembly 18. The transmitting elements 16 are generally embedded in the surface 20 of the surface assembly 18. In various examples, the transmitting elements 16 may be embedded in the top ticking 86 or between the top ticking 86 and the bottom ticking 88. The embedded transmitting elements 16 may be advantageous for reducing pressure on the patient disposed on the surface assembly 18. The transmitting elements 16 may be arranged in a matrix or array, as illustrated, or in various patterns. In different pattern examples, the concentration of transmitting elements 16 may differ based on common locations of the receiving assembly 28, common movement of the receiving assembly 28 based on patient movement (e.g., more transmitting elements 16 disposed near the seat of the patient than the foot of the patient), etc.

Referring again to FIG. 14, the sensor assembly 24 coupled to the patient may be the biometric sensor 180. The biometric sensor 180 may be coupled to the patient via a device, gown, patch, etc. The biometric sensor 180 may be configured as a blood pressure sensor, a glucose monitor, an electrocardiogram patch, a respiration rate monitor, etc. In various examples, multiple types of biometric sensors 180 may be disposed on the patient at any time. Depending on the configuration of the biometric sensor 180, the biometric sensor 180 may be coupled to the patient at different locations. The multiple biometric sensors 180 may be disposed in a single patch or location or in multiple locations. The location or locations of the biometric sensor 180 may be communicated to the controller 90 of the surface assembly 18 by a user input. Alternatively, the sensor assembly 24 may wirelessly communicate the type of biometric sensor 180 to at least one of the controller 22 of the support apparatus 10 and the controller 90 of the surface assembly 18, which may include stored locations associated with each type of sensor 26. Additionally or alternatively, the strength of the charging interface 162 may be utilized to determine the location of the receiving assembly 28. The location may be a location relative to the support apparatus 10, the location on the patient, or a combination thereof. The location may be utilized by the charging system 158 to selectively energize the closest transmitting elements 16.

Based on the type and/or location of the biometric sensor 180, different transmitting elements 16 may be energized. The transmission unit 192 may selectively direct energy to the transmitting elements 16 closest to the location of the sensor assembly 24, and consequently the receiving assembly 28. Accordingly, the sensor assembly 24 may be powered by a minimal amount of electromagnetic fields sufficient to power the sensor assembly 24.

Additionally or alternatively, at least one of the support apparatus 10 and the surface assembly 18 may include a weight or force sensor 194 for monitoring a position of the patient on the surface assembly 18. The force sensors 194 may be powered through the charging system 158. The transmission unit 192 may utilize position information received from the force sensor 194, alone or in combination with the location of the sensor assembly 24, to adjust which transmitting elements 16 are selectively energized. Accordingly, various "hot spots" of energized transmitting elements 16 may be created by the transmission unit 192 to power the sensor assembly 24. It is contemplated that the transmitting elements 16 may also be coupled to a top surface of the MCM system 138 and function in a similar manner as described with respect to the surface assembly 18 without departing from the teachings herein.

Referring again to FIG. 15, the charging system 158 is advantageous for minimizing or eliminating pressure on the patient supported on the support apparatus 10. An additional or alternative sensor 26, such as an interface pressure sensor 196, may be utilized with the charging system 158. The interface pressure sensor 196 may be directly coupled to the patient, such as through a bandage, or otherwise coupled to the patient, such as with a device, a gown, etc. In the illustrated example, the interface pressure sensor 196 is included in a sacral patch 198. Sacral patches 198 are generally adhered to a sacral region of the patient and are utilized to minimize or prevent pressure injuries from developing on the sacral region. In such examples, the interface pressure sensor 196 is configured to sense pressure at the interface between the patient and the surface assembly 18 or other supporting surfaces. The interface pressure sensor 196 may sense a force applied to an area and communicate the pressure data to the controller 22, as described herein. The interface pressure sensor 196 may be included in a similar patch or bandage in a different location to monitor other areas of the patient, particularly those more susceptible to the development of pressure injuries.

As the sacral patch 198 is worn on the sacral region, the transmission unit 192 may selectively energize the transmitting elements 16 that generally align with the sacral region of the patient. The transmitting elements 16 that correspond with the sacral region may be determined by or stored in the controller 90 of the surface assembly 18, the controller 22 of the support apparatus 10, or otherwise communicated to the transmission unit 192. Alternatively, the transmitting elements 16 may be energized based on information from the force sensors 194. It is contemplated that multiple transmitting elements 16 and multiple "hotspots" may be energized concurrently or independently based on the configuration of the sensor assembly 24 and locations of the various sensors 26, as well as other components to be powered. Further, various sensor assemblies 24, generally with independent receiving assemblies 28, may be worn by the patient and powered simultaneously or independently. It is contemplated that each sensor 26 may be operably coupled to an individual receiving assembly 28 or alternatively, one receiving assembly 28 may be operably coupled with multiple sensors 26, including sensors 26 of the same type and/or different types, without departing from the teachings herein.

Referring again to FIGS. 5-15, in examples where the sensors 26 are being powered, each sensor 26 may be activated at predetermined intervals to reduce power consumption and, consequently reduce electromagnetic fields used to power the sensors 26. For example, at each interval, the sensor 26 may receive power supplied from the transmitting element 16, sense or measure the respective data, transfer the data as described further herein, and return to a deactivated or sleep state. The predefined intervals may be any practicable interval and may be adjusted by the caregiver.

Figure 16:
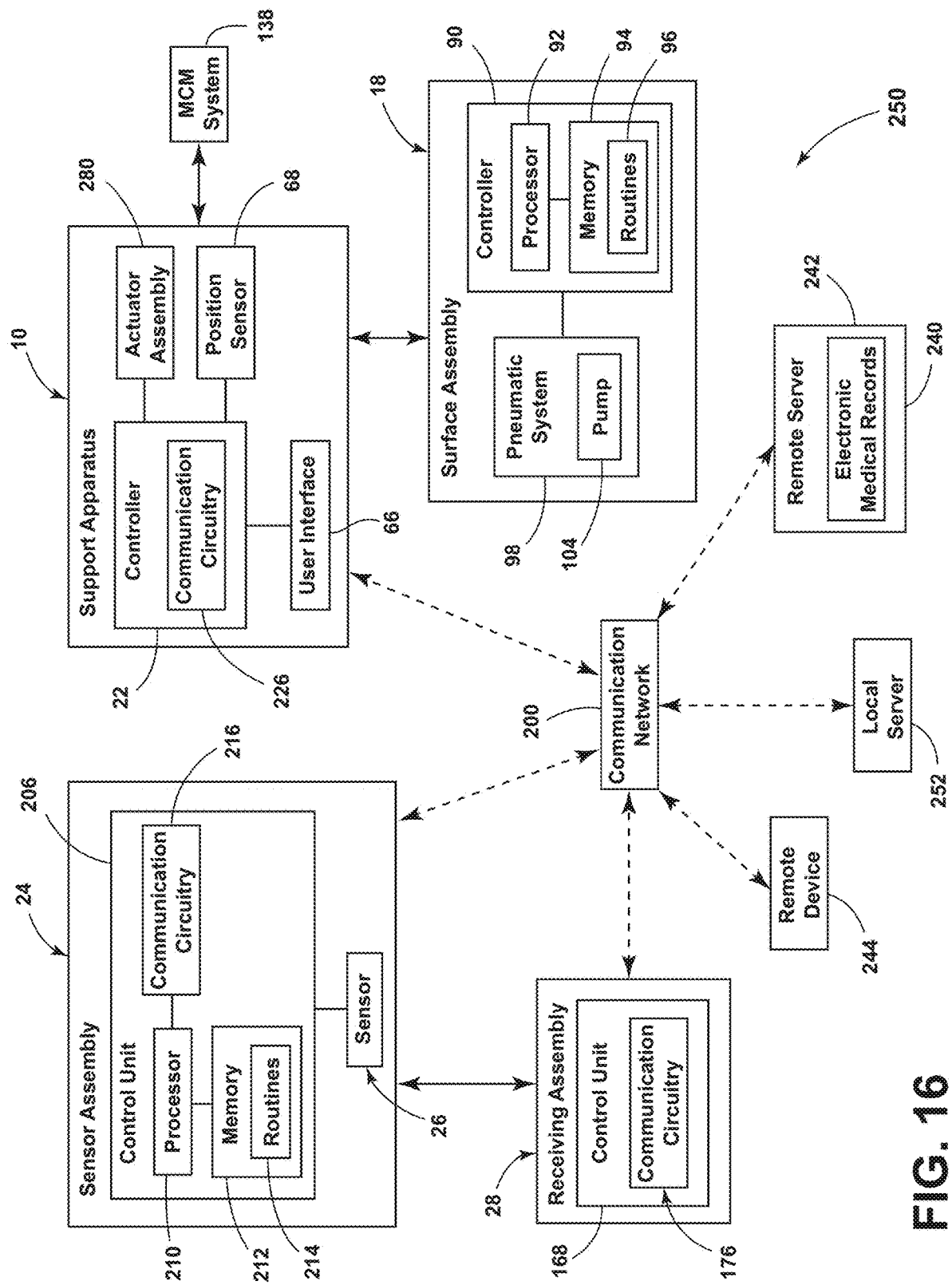
FIG. 16 is a block diagram of an information system for communicating data, according to the present disclosure.

Referring again to FIGS. 5 and 11, as well as FIG. 16, the powering of the various components described herein may be adjusted based on communication between the controller 22 of the support apparatus 10 and the receiving assembly 28. Data may be communicated between the control unit 168 and the controller 22 via the charging interface 162 and/or a secondary communication link that is powered by the charging system 158 (e.g., over a wireless communication network 200). The data transfer between the receiving assembly 28 and the controller 22 may be advantageous for adjusting the power transferred between the transmitting element 16 and the receiving element 30.

A magnitude of electromagnetic fields or waves generated between the receiving element 30 and the transmitting element 16 may be controlled or modulated by at least one of the control unit 168 and the controller 22. The electromagnetic waves may be modulated in response to the sensed coupling coefficient. At least one of the control unit 168 and the controller 22 may determine the coupling coefficient (e.g., the strength of the interaction) between the receiving element 30 and the transmitting element 16. The modulation may occur through direct communication within the charging system 158, or through the secondary communication link that is powered by the charging system 158 (e.g., the communication network 200).

The electromagnetic field may be adjusted until at least one of a minimum exposure level and a minimum energy storage level is reached. Modulation of the electromagnetic waves may minimize exposure of the patient to the electromagnetic waves. The inclusion of the storage feature 160 in the receiving assembly 28 reduces the magnitude of the energy in the power transfer at expense of up-time availability for the various components being powered. The exposure of the patient to the electromagnetic waves is generally minimized, such that pacemakers and other implanted devices are not substantially impacted by the charging system 158. The electromagnetic waves may also be modulated to provide sufficient energy to the receiving element 30 based on the coupling coefficient to provide a minimum amount of power to support the operation of the corresponding component. For example, the electromagnetic waves may be increased when a poor coupling coefficient is detected. It is contemplated that the amount of energy utilized to power certain components may determine how often the powered component may be activated.

Additionally or alternatively, the control unit 168 may monitor power transfer information and communicate the power transfer information to the controller 22. The power transfer information may include the coupling coefficient or an amount of energy being received at the receiving element 30, which may be a sensed voltage level. The control unit 168 may monitor the voltage level and communicate the voltage level to the controller 22. The control unit 168 may store a predefined voltage level to be received for powering the various components. The predefined voltage may differ based on what component is being powered (e.g., the sensor assembly 24 compared to the pump 104, etc.). The control unit 168 may also communicate information to the controller 90 of the surface assembly 18, which may be advantageous for configurations where the receiving assembly 28 is coupled to the surface assembly 18. In such examples, the controller 90 may communicate the information with the controller 22 of the support apparatus 10.

If the voltage being received by the receiving assembly 28 is below the predefined voltage level, the controller 22 may respond by increasing an intensity of the transmitting element 16 to generate more energy. In such circumstances, a greater loss of power may occur but the receiving assembly 28 may receive sufficient energy to power the various components. If the voltage being received by the receiving assembly 28 is above the predefined level, the intensity of the transmitting element 16 may be reduced to minimize energy loss and exposure of the patient to electromagnetic waves. In this way, the charging system 158 is adaptive based on the coupling between the transmitting element 16 and the receiving element 30. It is contemplated that the predefined level may be a single energy level or an energy level range.

Figure 5:
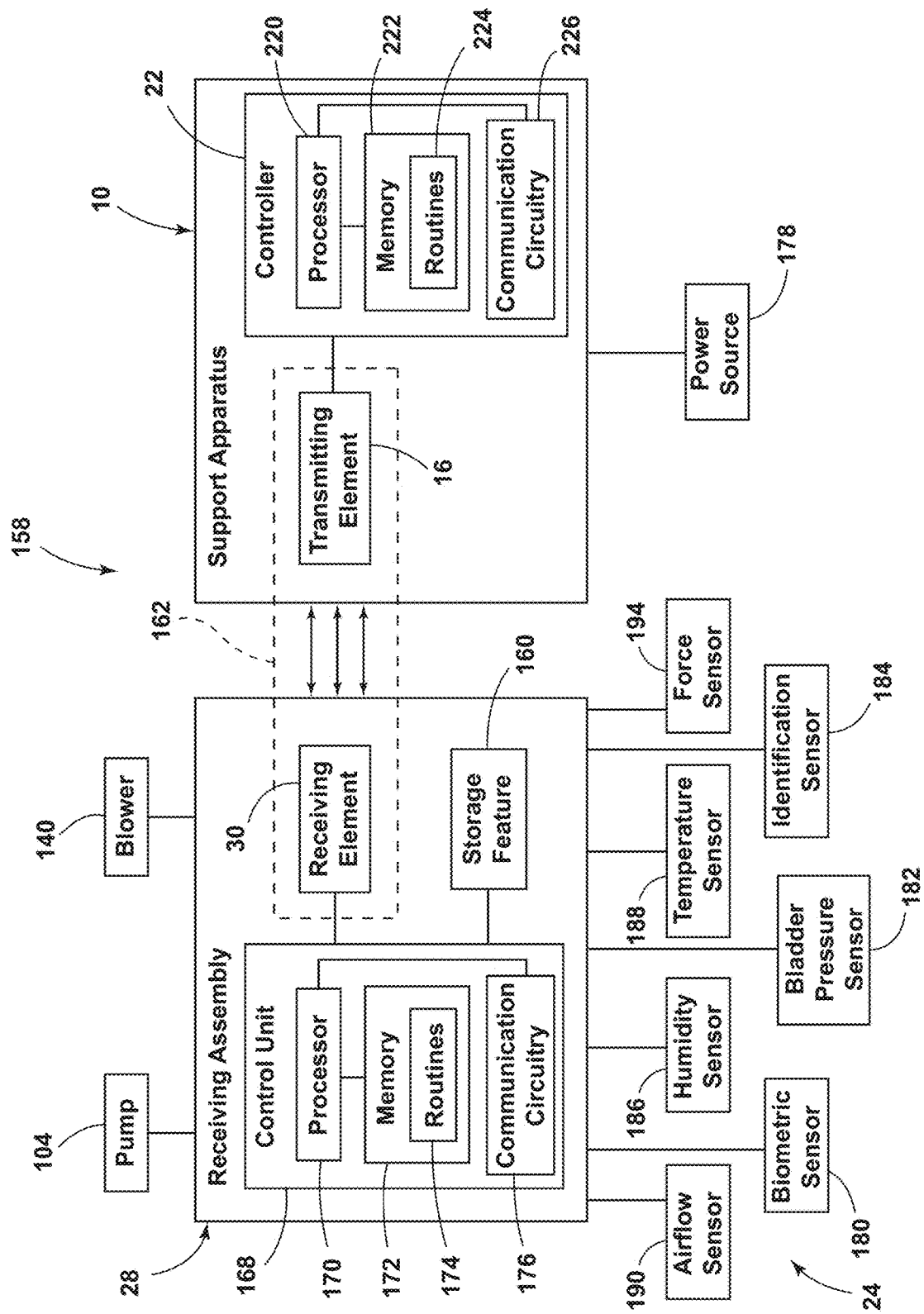
FIG. 5 is a block diagram of a charging system with a transmitting element coupled to a support apparatus, according to the present disclosure.

Referring still to FIGS. 5, 11, and 16, the control unit 168 is communicatively coupled to the storage feature 160 and may determine a current energy or charge level. The control unit 168 may compare the current energy level to a predefined energy threshold or predefined charge level. When the current energy level stored in the storage feature 160 reaches the predefined energy threshold, the sensor assembly 24 may initiate wireless data transfer as described herein. At least one of the controller 22 and the control unit 168 may control the power and data transfer between the receiving assembly 28 and the support apparatus 10 or the surface assembly 18 in response to the coupling coefficient. One or both of the power transfer and the data transfer may be conducted over varying time intervals controlled by the local coupling coefficient based on alignment between the transmitting element 16 and the receiving element 30. When the coupling coefficient reaches a predefined level or strength, the power transfer and the data transfer may be started. Alternatively, the power transfer may start at a first predefined level, and the data transfer may start at a second predefined level. In certain aspects, the second predefined level may be higher than the first predefined level allowing power transfer to occur with a lower coupling coefficient than data transfer.

Referring still to FIG. 16, the various configurations of the sensor assembly 24 are each configured to wirelessly transmit sensed data. The wireless transmission of data reduces wiring in components used to care for the patient, which may assist in reducing pressure injury development. The wireless transmission of data is also advantageous for communicating information about the patient or treatment for the patient to the caregiver.

The sensors 26 in the charging system 158 are configured to sense a variety of surface information and patient information. For example, the sensors 26 are configured to sense at least one of, but not limited to, airflow, temperature, humidity, blower speed, bladder pressure, patient immersion, type of surface assembly 18, interface pressure, glucose, blood pressure, heart rate, respiration rate, skin conductivity, blood surface, saturation $O_2$, respiration rate, thoracic sounds, etc. The patient and surface information assist in providing care for the patient and controlling and/or monitoring performance functionality of the surface assembly 18.

In certain aspects, the sensor assembly 24 includes the sensor 26 in communication with a control unit 206. The sensor 26 may be configured as any one or more of the biometric sensor 180, the bladder pressure sensor 182, the identification sensor 184, the interface pressure sensor 196, the airflow sensors 190, the humidity sensor 186, and the temperature sensor 188. The control unit 206 includes a processor 210, a memory 212, and other control circuitry. Instructions or routines 214 are stored within the memory 212 and executable by the processor 210. The control circuitry includes communication circuitry 216 for communicating with the controller 22 of the support apparatus 10. The control unit 206 receives the sensed data from the various sensors 26 and communicates the sensed data to the controller 22 of the support apparatus 10 via the communication network 200. It is also contemplated that the sensor assembly 24 may be operably coupled with the control unit 168 of the receiving assembly 28, without the separate control unit 206, without departing from the teachings herein. In such examples, the control unit 168 has the structure and performs the functions described herein with respect to the control unit 206.

The controller 22 of the support apparatus 10 is communicatively coupled with the control unit 206 of the sensor assembly 24. The controller 22 has a processor 220, a memory 222, and other control circuitry. Instructions or routines 224 are stored within the memory 222 and executable by the processor 220. The control circuitry includes communication circuitry 226 for communicating via the communication network 200. In various examples, the controller 22 receives the sensed data from the sensor assembly 24, either directly, through the control unit 206, and/or through the communication network 200, and may adjust the support apparatus 10 or the charging system 158 in response to the sensed data.

Additionally, one or both of the control unit 206 of the sensor assembly 24 and the controller 22 of the support apparatus 10 may communicate the sensed data to at least one of an electronic medical record (EMR) 240 often stored in a remote server 242 and a remote device 244 for viewing by the caregiver. The sensed information may be communicated to an information system 250 to be viewed by the caregiver treating the patient. It is contemplated that other types of sensors 26 may be utilized within the charging system 158 without departing from the teachings herein.

According to various aspects, the biometric sensor 180 may monitor various physiological attributes (e.g., the biometric data) of the patient, including, for example, heart rate, respiration rate, blood pressure, glucose, skin conductivity, blood surface, saturation $O_2$, respiration rate, thoracic sounds, etc. The biometric data may be monitored by the caregiver, allowing the caregiver to monitor the status of the patient and provide treatments in response. The biometric data may be communicated to the controller 22 and subsequently stored in the EMR 240 and/or viewed on the application interface 150 (FIG. 15). Further, the biometric data may be utilized to trigger various alerts when the biometric data is outside of a predefined range or a change in the biometric data is outside a predefined change range.

Based on the sensed biometric data, the support apparatus 10 may be adjusted to a certain position (e.g., elevated head region, etc.). The caregiver may adjust the support apparatus 10, or alternatively the support apparatus 10 may automatically adjust to a predefined position based on the sensed data. The support apparatus 10 includes an actuation assembly 280, which may adjust the upper frame 44 relative to the base frame 46 and/or the segments 48, 50, 52 of the upper frame 44 relative to one another. For example, based on heart or respiration rate data, the head end of the support apparatus 10 may be elevated.

Referring still to FIG. 16, the sensor assembly 24 with the bladder pressure sensors 182 associated with the pneumatic system 98 may provide more accurate information for determining pressure to be utilized for various pressure therapies. For example, when the pneumatic system 98 is activated by the caregiver, the bladders 106 may be independently adjusted between the deployed state and the non-deployed state. The bladder pressure sensors 182 may continually sense the pressure within the bladders 106 and the sensed pressure data may be communicated to the controller 22 of the support apparatus 10. The support apparatus 10 may adjust the position of the frame 12 to maximize the pressure therapy.

In certain aspects, the fluid in the bladders 106 may be continually adjusted in response to the sensed data, which may be part of a continuous low pressure therapy. For example, the increase in pressure within select bladders 106 may be correlated to an increased or decreased weight or force that results from the patient moving positions. The bladders 106 may be adjusted to a predefined pressure or pressure range in response to the movement of the patient. Further, the caregiver may monitor the condition of the patient in response to a fill or inflation level of the bladders 106 separate from and during therapies. The caregiver may adjust the amount of fluid within the bladders 106 to provide greater comfort to the patient or to adjust the pressure applied via the therapies. The sensed pressure and change in sensed pressure may be monitored by the caregiver to determine the effectiveness of the selected pressure therapy, as well as the comfort of the patient. Additionally or alternatively, the sensed pressure information may be communicated to the remote server 242 and stored within the EMR 240.

Referring still to FIG. 16, the interface pressure sensor 196 may be utilized to monitor the potential development of pressure injuries by sensing pressure applied to certain body regions. For example, when the support apparatus 10 has an elevated head region, for example, a 30° angle of elevation, weight is shifted to a hip or pelvis area of the patient, which may contribute to pressure injury development in the sacral region. A pressure injury is localized damage to the skin and underlying soft tissue. Generally, the pressure injury is developed over a bony prominence and may be related to the use of a medical or treatment device. Pressure injuries develop as a result of intense pressure, prolonged pressure, pressure in combination with shear, or a combination thereof. The sensor assembly 24 may sense a magnitude of the pressure on a specific region of the patient, for example, the sacral region, as well as duration of the pressure.

The sensed pressure may be communicated to the controller 22. In response to the sensed pressure data, the controller 22 of the support apparatus 10 may activate the actuation assembly 280 to adjust the position of the upper frame 44 to reduce pressure on certain body areas. Additionally or alternatively, the controller 22 may communicate with the surface assembly 18 to activate the pneumatic system 98 in accordance with information from the EMR 240 (e.g., stored pressure therapies). The controller 22 may also generate an alert that the patient may be at risk for developing a pressure injury.

Additionally or alternatively, the identification data sensed by the identification sensor 184 may be utilized to control the function of the support apparatus 10. For example, when the non-powered surface assembly 80 is utilized, the support apparatus 10 may have a greater range of articulation between the segments 48, 50, 52 of the upper frame 44. If the powered surface assembly 82 then replaces the non-powered surface assembly 80, the support apparatus 10 may adjust the position of the upper frame 44 to a shallower incline, for example, to maximize the effect of the bladders 106 in the pneumatic system 98.

Further, the position information from the position sensor 68 of the support apparatus 10 may affect the function of the surface assembly 18. For example, if the head region is elevated, turn assist protocols may not be activated in the surface assembly 18, as turning the patient in the elevated head position may result in discomfort to the patient or less effective therapy results. Accordingly, the identification information from the sensor assembly 24 and the information from the position sensor 68 may alter functions of the support apparatus 10 and/or the surface assembly 18.

Referring still to FIG. 16, the data communication between various devices may be conducted via the communication network 200. The communication network 200 may be part of a network of the medical facility. The network may include a combination of wired connections, as well as wireless connections, which may include the wireless communication network 200. The communication network 200 includes a variety of electronic devices, which may be a combination of various wired or wireless communication protocols. The communication network 200 may be implemented via one or more direct or indirect nonhierarchical communication protocols, including but not limited to, Bluetooth®, Bluetooth® low energy (BLE), Thread, Ultra-Wideband, Z-wave, ZigBee, etc.

Additionally, the communication network 200 may correspond to a centralized hierarchal communication network 200 where one or more of the devices communicate via a router (e.g., a communication routing controller). The communication network 200 may be implemented by a variety of communication protocols including, but not limited to, global system for mobile communication (GSM), general packet radio services, code division multiple access, enhanced data GSM environment, fourth generation (4G) wireless, fifth generation (5G) wireless, Wi-Fi, world interoperability for wired microwave access (WiMAX), local area network, Ethernet 262, etc. By flexibly implementing the communication network 200, various devices and servers may communicate with one another directly via the wireless communication network 200 or a cellular data connection.

The controllers and control units disclosed herein may include various types of control circuitry, digital or analog, and may each include the processor, a microcontroller, an application specific circuit (ASIC), or other circuitry configured to perform the various input or output, control, analysis, or other functions described herein. The memories described herein may be implemented in a variety of volatile and nonvolatile memory formats. Routines include operating instructions to enable various methods described herein.

Figure 17:
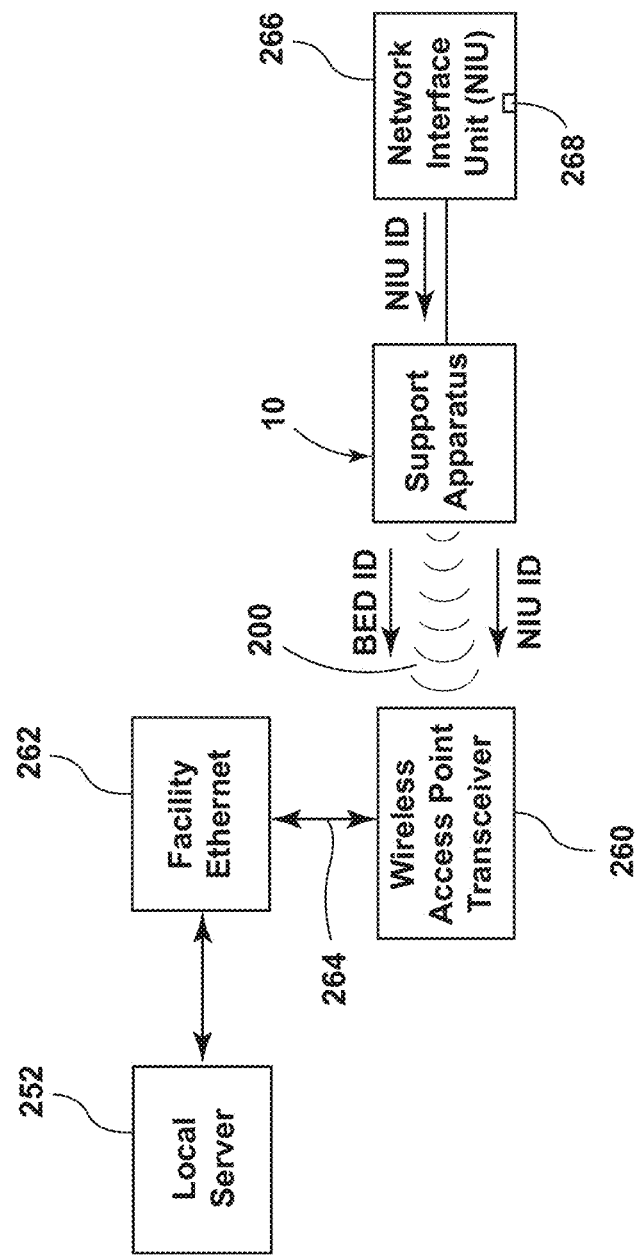
FIG. 17 is a block diagram of a support apparatus wirelessly communicating with a local server via a wireless access transceiver, according to the present disclosure.
Figure 18:
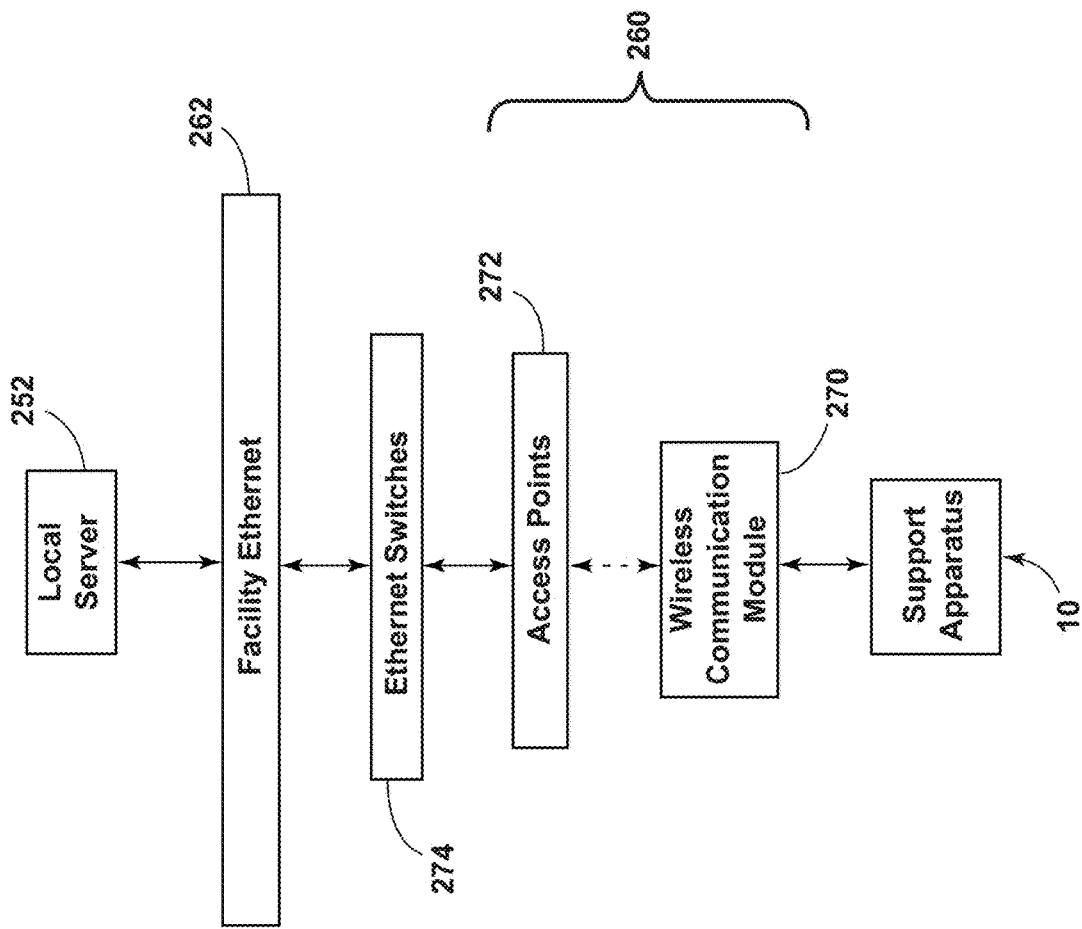
FIG. 18 is a block diagram of a support apparatus wirelessly communicating with a local server via wireless access points, according to the present disclosure.

Referring still to FIG. 16, as well as FIGS. 17 and 18, the support apparatus 10 is configured to communicate data, which may include the sensed data from the sensor assembly 24, charging information (e.g., the coupling coefficient, charge level, etc.), etc., to the information system 250 of the medical facility. A local server 252 may include software related to the information system 250. The remote device 244 and the remote server 242 may also be in communication with the information system 250 to receive the information from the support apparatus 10 and send additional information.

Exemplary communications of the support apparatus 10 to the local server 252 are illustrated. In certain aspects, the support apparatus 10 is configured to communicate with a wireless access transceiver 260, which is coupled to Ethernet 262 of the medical facility, the communication network 200 provides for bidirectional communication between the support apparatus 10 and a wireless access transceiver 260. The wireless access transceiver 260 communicates directly with Ethernet 262 via a data link 264.

As illustrated in FIG. 17, the support apparatus 10 may be associated with a network interface unit 266. Multiple network interface units 266 may be provided in various locations of the medical facility. The support apparatus 10 and network interface units 266 are each assigned a unique identification code, such as a serial number. The local server 252, or another aspect of the information system 250, may include software that operates to associate the identification code of the support apparatus 10 with identification data of the network interface unit 266 to locate the support apparatus 10 within the medical facility. Each network interface unit 266 includes a port 268 for selectively coupling with Ethernet 262. When the network interface unit 266 is coupled with Ethernet 262, the network interface unit 266 communicates the identification data to the support apparatus 10, which then wirelessly communicates the data for the support apparatus 10 and the network interface unit 266 to the wireless access transceiver 260. The wireless access transceiver 260 then communicates with the local server 252 via Ethernet 262.

As illustrated in FIG. 18, the support apparatus 10 may be capable of communicating wirelessly via a wireless communication module 270. The wireless communication module 270 generally communicates via an SPI link with circuitry of the associated support apparatus 10 (e.g., the communication circuitry 226) and via wireless a wireless 802.11 link with wireless access points 272. Wireless access points 272 are generally coupled to Ethernet switches 274 via 802.3 links. It is contemplated that the wireless communication modules 270 may communicate with the wireless access points 272 via any of the wireless protocols described herein. Additionally or alternatively, the Ethernet switches 274 generally communicate with Ethernet 262 via 802.3 links. Ethernet 262 is also engaged with the local server 252, allowing information to be communicated between the local server 252 and the support apparatus 10.

Referring again to FIG. 16, as well as to FIGS. 19-23, the support apparatus 10 is generally in communication with the remote device 244. The remote device 244 includes an application or software for displaying the application interface 150. The remote device 244 may be a phone, a tablet, a wearable device, a laptop, or other devices and may belong or be assigned to the caregiver. The application interface 150 may also be displayed on the user-interface 66 (FIG. 1), devices in nurse call stations, status boards, etc. without departing from the teachings herein.

The remote device 244 may be associated with the information system 250 for sharing information and communicating information between caregivers. The remote device 244 includes the application interface 150 to display information from the EMR 240, the sensor assembly 24, the support apparatus 10, the charging system 158, or a combination thereof. In certain aspects, the controller 22 of the support apparatus 10 is configured to generate notifications and alerts configured to be communicated to the remote device 244 to be viewed on the application interface 150.

Figures 19, 20:
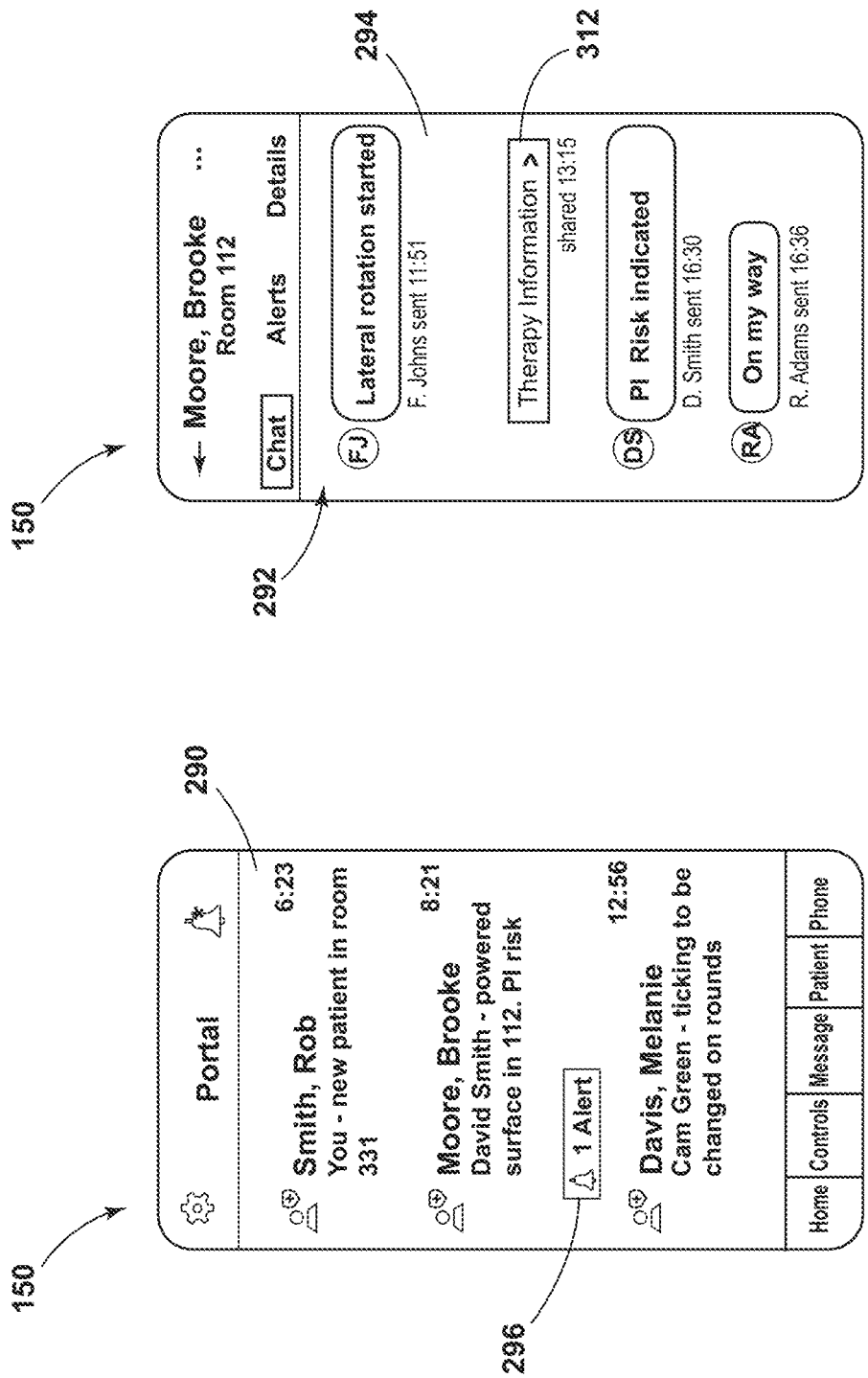
FIG. 19 is representative of an application interface showing patient profiles, according to the present disclosure.
FIG. 20 is representative of an application interface showing a chat feature of a patient profile, according to the present disclosure.

As illustrated in FIG. 19, the application interface 150 is configured to display a communication portal 290, including patient profiles 292 that can be accessed through the communication portal 290. Each patient profile 292 corresponds to one patient associated with the caregiver. Each caregiver associated with the patient is granted access to the respective patient profiles 292. Additionally or alternatively, the communication portal 290 provides a way for each caregiver associated with the patient to communicate with one another, as well as a way to receive and communicate updates about the patient.

As illustrated in FIG. 20, an exemplary patient profile 292 is illustrated on the application interface 150. The caregivers may directly message one another through a chat feature 294 and may communicate information stored within the EMR 240. This communication may be stored within the remote device 244 and may be stored within the EMR 240. Alternatively, the chat feature 294 may be utilized for sharing information that is not be stored in the EMR 240 of the patient. The chat feature 294 in the communication portal 290 may also provide for sharing information from the sensor assembly 24.

Referring again to FIG. 19, as well as FIGS. 21 and 22, the controller 22 of the support apparatus 10 may be configured to generate an alert feature 296 in response to sensed information received from the sensor assembly 24. The alert feature 296 may be viewed on the communication portal 290, as illustrated in FIG. 19, or as a push notification, as illustrated in FIG. 22. The visual alert feature 296 on the application interface 150 may be advantageous for alerting caregivers of information relating to the patient and/or the support apparatus 10.

According to various aspects, information related to the alert feature 296 may be viewable on an alerts view 298 of the application interface 150, as illustrated in FIG. 21. For example, the controller 22 may generate the alert in response to the pressure data from the interface pressure sensor 196 or the biometric data sensed by the biometric sensor 180. In the example of FIG. 21, the alert is related to the risk of developing a pressure injury. The application interface 150 displays an interface pressure, a current time that the sensed pressure has been sustained, and a total amount of time the pressure has been sensed over a predefined period. The type of information illustrated in FIG. 21 is merely exemplary and not meant to be limiting. Depending on the treatment of the patient, preferences of the caregiver, and the type of alert, the alerts view 298 may include a variety of information to assist the caregiver in treating the patient.

Additionally, in the illustrated example of FIG. 21, the application interface 150 includes selectable features, such as an EMR feature 300 and a therapy activation feature 302. The caregiver may select the EMR feature 300 to view information obtained from the EMR 240 of the patient in the remote server 242. The EMR information may also be stored in the local server 252. The therapy activation feature 302 may activate the pneumatic system 98 or other devices associated with the support apparatus 10. The caregiver may utilize the alert generated in response to data from the sensor assembly 24 to adjust a function or position of the support apparatus 10, the surface assembly 18, the MCM system 138, or a combination thereof.

Referring to FIG. 22, in another example, the controller 22 may generate an alert when the biometric data sensed by the biometric sensor 180 is outside of the predefined range. The alert feature 296 illustrated in FIG. 22 is the push notification, which may be advantageous for when the remote device 244 is not actively displaying the patient profiles 292. The application interface 150 may provide a visual, audible, and/or haptic alert on the remote device 244 or through a nurse call station.

Figure 23:
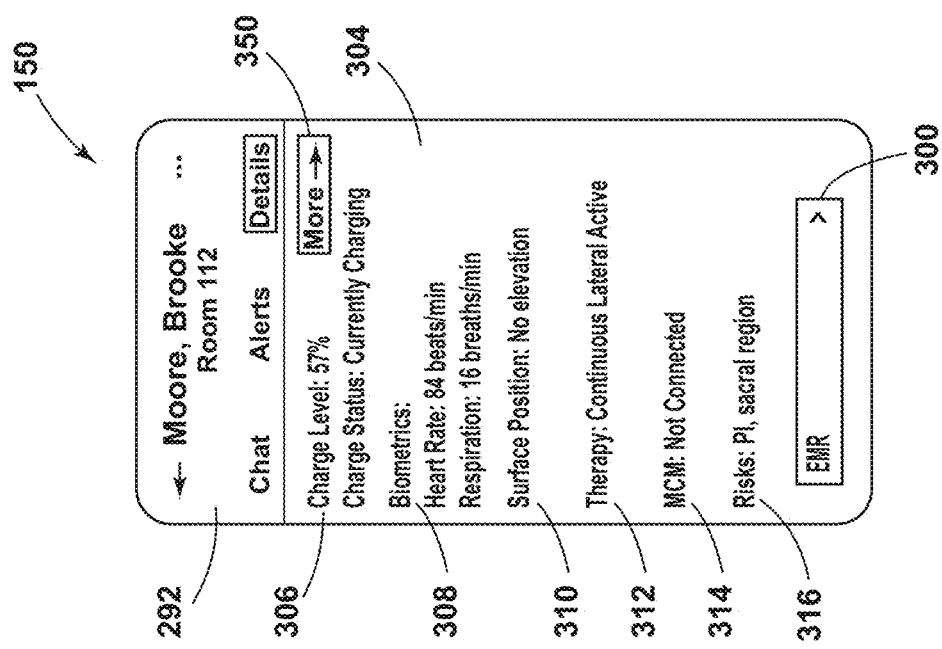
FIG. 23 is representative of an application interface showing a detailed view of information from various sensors, according to the present disclosure.

Referring to FIG. 23, the application interface 150 may include a detailed view 304 for displaying detailed information related to the patient and devices associated with the patient (e.g., the support apparatus 10, the surface assembly 18, the sensor assembly 24, the receiving assembly 28, etc.). In the illustrated example of FIG. 23, the detailed view 304 of the application interface 150 generally includes information from the receiving assembly 28, such as a charge indicator 306. For example, the control unit 168 of the receiving assembly 28 may communicate the current charge level of the storage feature 160 to the controller 22, which is configured to generate a notification to be viewed on the application interface 150. The application interface 150 may then display the current charge level and the current charge status (e.g., charging, not charging, etc.) as part of the charge indicator 306. The charge indicator 306 may be advantageous for the caregiver to monitor the charge of the receiving assembly 28, allowing the caregiver to adjust the position of the receiving element 30 when the charge level is low.

Additional information that is included on the example application interface 150 in FIG. 23 includes biometric information 308, such as heart rate and respiration rate. Additionally, in the illustrated example, surface assembly 18 or support apparatus information 310, therapy information 312, and MCM information 314 are also displayed. Further, risk information 316 may be included on the application interface 150. Information from the sensor assembly 24, the surface assembly 18, and the support apparatus 10 may be communicated to the caregiver via the application interface 150. It is contemplated also the control unit 206 of the sensor assembly 24 and/or the control unit 168 of the receiving assembly 28 may communicate directly with the information system 250. The information on the detailed view 304 is merely exemplary and not meant to be limiting. Additional information or additional views of information may be utilized without departing from the teachings herein.

Figure 24:
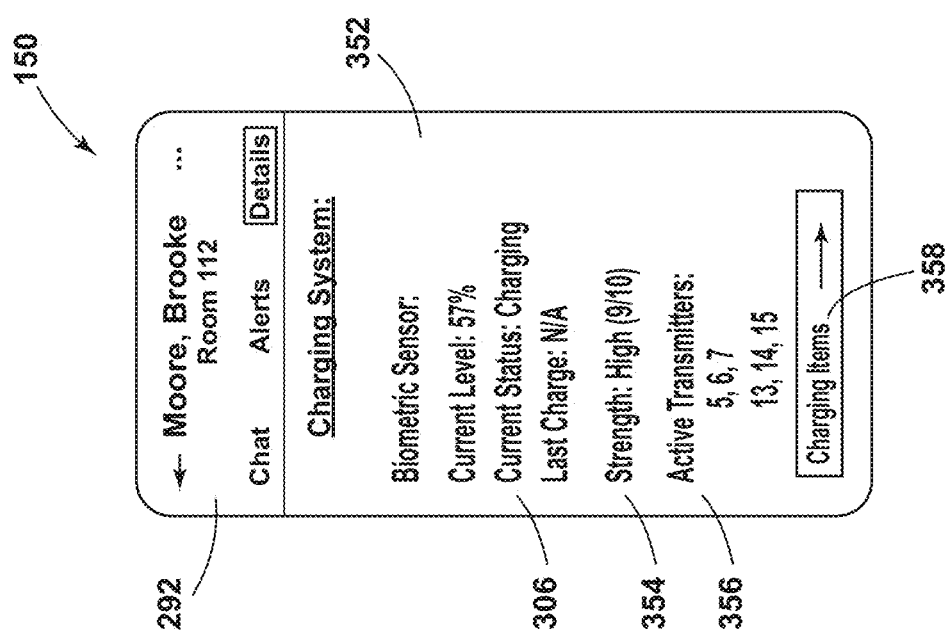
FIG. 24 is representative of an application interface showing detailed information related to active components of a charging system, according to the present disclosure.

Referring to FIG. 24, the caregiver may select an icon 350 (e.g., "More") on the detailed view 304 in FIG. 23, which provides additional details about the charging system 158, as illustrated in FIG. 24. A charging detailed view 352 may be displayed on the application interface 150, which includes a variety of information and features related to the charging system 158. For example, the charging detailed view 352 in the illustrated example includes the charge indicator 306, listing the current level of charge, the current charge status, and information about a last charge.

Additionally, the charging detailed view 352 may include a strength indicator 354, generally indicative of the coefficient strength between the transmitting element(s) 16 and/or the receiving element(s) 30 for the select component (e.g., the component associated with the receiving element 30). The strength indicator 354 may be a scaled number (e.g., "x" value out of a predefined value), a category (e.g., high, low, etc.), or both. The strength indicator 354 may assist the caregiver in determining if and how to adjust the charging system 158. For example, the strength indicator 354 may allow the caregiver to determine whether the receiving assembly 28 for a certain component is receiving sufficient power, whether the receiving assembly 28 should be moved closer to the active transmitting element 16, whether additional or alternative transmitting elements 16 should be activated, etc. The charging detailed view 352 may also include transmitter information 356, indicating which transmitting elements 16 are currently active.

In the example illustrated in FIG. 24, the charging detailed view 352 includes information about the biometric sensor 180. The charging detailed view 352 may include information related to one, several, or each component operably coupled with the receiving assembly 28 or receiving assemblies 28, as well as the transmitting elements 16. This may be advantageous for the caregiver to monitor the charging system 158.

Figure 25:
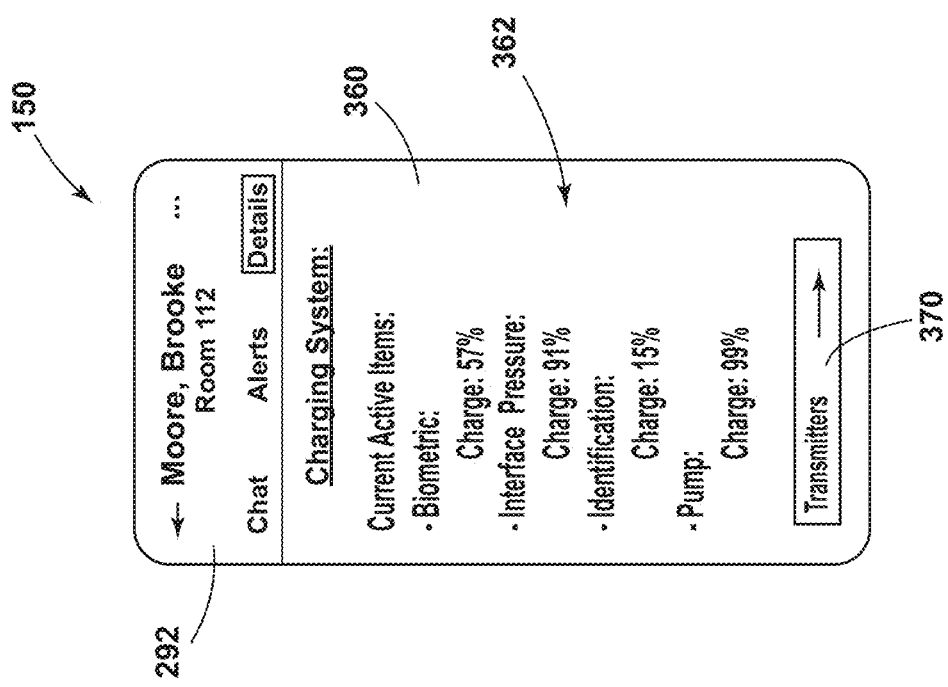
FIG. 25 is representative of an application interface showing detailed information about active components and charge levels of a charging system, according to the present disclosure.

Referring to FIG. 25, upon selecting a charging items icon 358 on the charging detailed view 352 (FIG. 24), the application interface 150 may display an overall charging view 360. The overall charging view 360 may provide a summary or overview of the components included in the charging system 158. For example, the overall charging view 360 illustrated in FIG. 25 includes a list 362 of the components that are active and/or in use in the charging system 158, as well as a current charge level (e.g., a percentage). The overall charging view 360 may also include additional or alternative information including charge status, charging-related alerts (e.g., no charging interface 162 or poor coupling coefficient), inactive components, etc. The overall charging view 360 may also include a transmitter icon 370 that guides the caregiver to information about the transmitting elements 16.

Figure 26:
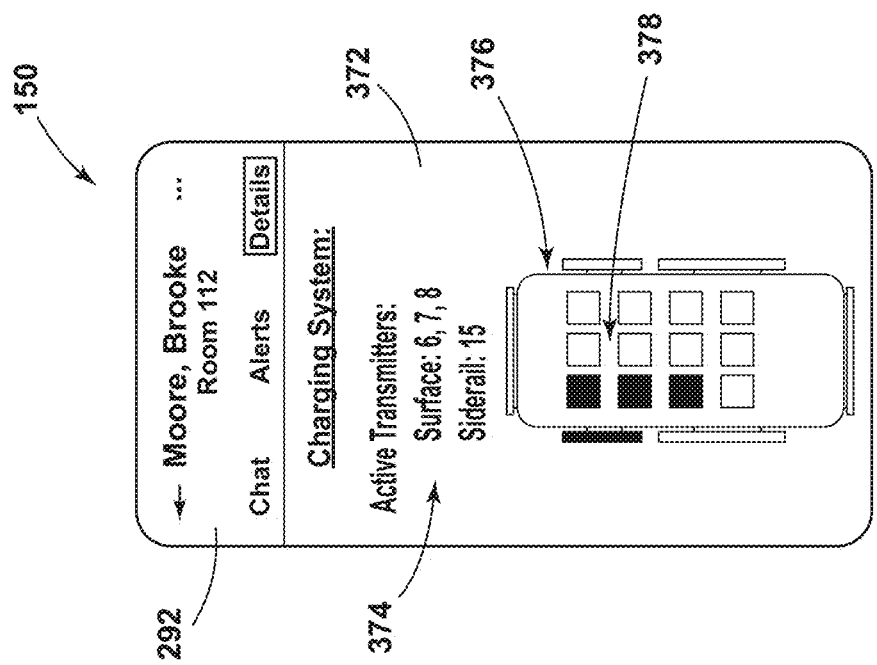
FIG. 26 is representative of an application interface showing detailed information related to transmitting elements of a charging system, according to the present disclosure.

Referring to FIG. 26, the application interface 150 may display a transmitter view 372, including a variety of information about the transmitting elements 16 of the charging system 158. In the example illustrated in FIG. 26, the transmitter view 372 includes a list 374 of the active transmitting elements 16, which may include those currently charging the corresponding receiving assembly 28 or receiving assemblies 28. The active transmitting elements 16 may be arranged by location on the support apparatus 10 (e.g., head end, frame 12, surface assembly 18, etc.).

Further, the transmitter view 372 may include a graphic 376, which shows the activation status for each of the transmitting elements 16 on the support apparatus 10. The graphic 376 generally includes a graphical representation of the support apparatus 10 including one or more of the surface assembly 18, the siderails 58, 60, 62, 64, the headboard 54, the footboard 56, the MCM system 138, and/or any other location with transmitting elements 16. The graphic 376 also includes transmitter indicators 378 for each transmitting element 16 on the support apparatus 10. The graphic 376 is configured to distinguish the active transmitting elements 16 from the inactive transmitting elements 16 via the transmitter indicators 378. The active transmitting elements 16 may be identified or distinguished by highlighting or otherwise differentiating the transmitter indicators 378 that correspond to the active transmitting elements 16 from the transmitter indicators 378 that correspond to the inactive transmitting elements 16. The caregiver may also adjust which transmitting elements 16 are active from the application interface 150 by selecting or de-selecting the transmitter indicators 378.

Referring to FIGS. 1-26, the sensor assembly 24 provides wireless sensors 26 that allow for more convenient and efficient care for the patient, as well as information about the functionality and performance of the surface assembly 18. The sensor assembly 24 and the receiving assembly 28 disclosed herein may be physically decoupled from the support apparatus 10. This may be advantageous for more conveniently adjusting, replacing, or removing the surface assembly 18. Further, different configurations of the surface assembly 18, such as the surface assembly 18, including the non-powered surface assembly 80 and the powered surface assembly 82, the MCM system 138, a mattress pad, incontinence pads, other support devices, etc. may be more conveniently interchanged. Decoupling the receiving assembly 28 increases ease of installation of the surface assembly 18, as well as allows for more convenient cleaning, disconnecting, and interchanging surface assemblies 18 and other supporting surfaces.

The wireless receiving assembly 28 may be positioned proximate to the transmitting element 16 to transfer power without substantially affecting the performance of the MCM system 138 and interface pressure between the patient and the supporting surface assembly 18. The transmitting element 16 may be coupled to the supporting surface 14, the siderails 58, 60, 62, 64, the surface assembly 18, or another practicable location to provide continuous wireless charging for the receiving assembly 28. Further, the charging system 158 may allow for tolerances due to poor coupling coefficients due to movement of the patient.

The charging system 158 may have a variety of configurations to power multiple components. For example, transmitting elements 16 may be coupled to the supporting surface 14, one or more siderails 58, 60, 62, 64, the headboard 54, the footboard 56, the surface assembly 18, the MCM system 138, a combination thereof, or various combinations thereof. Having multiple transmitting elements 16 provides flexibility in powering different components or components in different locations. Further, for sensor assemblies 24 coupled to the patient, having multiple transmitting elements 16 may be advantageous to continue to power the sensor assemblies 24 as the patient moves. Further, the transmitting elements 16 may be coupled to support apparatus to interact with receiving assemblies 28 in the surface assembly 18 in combination with transmitting elements 16 coupled to the surface assembly 18 to interact with receiving assemblies 28 coupled to the patient.

Use of the present devices and systems may provide for a variety of advantages. For example, the sensor assembly 24, the pump 104 of the pneumatic system 98, and the blower 140 of the MCM system 138 may be charged wirelessly. The components may be charged individually, in combination, or in various combinations. Further, the receiving assembly 28 includes the receiving element 30, which is configured to selectively interact with the transmitting element 16 of the support apparatus 10. The receiving element 30 is configured to interact via at least one of capacitive coupling and inductive coupling with the transmitting element 16. Moreover, the transmitting element 16 being coupled to the support apparatus 10 allows continual charging for the receiving assembly 28, thereby continually powering various components associated with the support apparatus 10. Further, the sensor assembly 24 may wirelessly transmit data about the patient and/or the surface assembly 18 to the support apparatus 10, which may affect the operation of the support apparatus 10 and provide information to the caregiver. Additionally, the receiving assembly 28 includes the storage feature 160 for storing sufficient energy for powering the various components and accessories while remaining small enough in size to minimize the risk of developing pressure injuries on the patient. Additional benefits and advantages may be realized and/or achieved.

The system disclosed herein is further summarized in the following paragraphs and is further characterized by combinations of any and all of the various aspects described therein.

According to another aspect of the present disclosure, a patient support apparatus includes a frame having a supporting surface. A transmitting element is coupled to the frame. A surface assembly is selectively positioned on the supporting surface. The surface assembly includes a surface selectively enclosing an interior. A controller is communicatively coupled to the transmitting element. A sensor assembly is coupled to the surface assembly. The sensor assembly includes a sensor configured to sense information about at least one of the surface assembly and a person positioned on the surface assembly. A receiving assembly is operably coupled to the surface assembly and the sensor assembly. The receiving assembly is configured to selectively interact with the transmitting element via a charging interface to power the sensor assembly.

According to another aspect, a sensor assembly includes communication circuitry configured to communicate sensed information to a controller via a wireless communication network.

According to another aspect, a receiving assembly includes a storage feature operably coupled to a receiving element of a receiving assembly to store energy to power a sensor assembly.

According to another aspect, a storage feature is a supercapacitor.

According to another aspect, a sensor is a biometric sensor coupled to a surface of a surface assembly.

According to another aspect, a sensor is coupled to a surface of the surface assembly and configured to sense patient information. The patient information includes at least one of heart rate, respiration rate, skin conductivity, blood surface, saturation $O_2$, respiration rate, and thoracic sounds.

According to another aspect, a biometric sensor senses biometric data from a person on a support apparatus.

According to another aspect, biometric data includes at least one of a heart rate and a respiration rate.

According to another aspect, a surface assembly includes a pneumatic system having a bladder operable between a deployed state and a non-deployed state.

According to another aspect, a sensor is a pressure sensor operably coupled with a bladder and configured to sense pressure within the bladder.

According to another aspect, a sensor is an identification sensor configured to communicate data to a controller. The data includes a type of surface assembly.

According to another aspect, energy transferred via a charging interface is adjusted in response to a type of surface assembly.

According to another aspect, at least one of a controller and a control unit of a receiving assembly is configured to determine a coupling coefficient between a transmitting element and a receiving element of a receiving assembly.

According to another aspect, at least one of a controller and a control unit is configured to modulate a magnitude of electromagnetic fields generated between a transmitting element and a receiving element based on a coupling coefficient.

According to another aspect, a transmitting element and a receiving assembly are configured to selectively interact via at least one of inductive coupling and capacitive coupling.

According to another aspect, a sensor is configured to sense surface information including at least one of airflow, temperature, humidity, blower speed, bladder pressure, patient immersion, and a type of surface assembly.

According to another aspect, a microclimate management system is operably coupled with a sensor assembly. The sensor assembly is configured to sense at least one of airflow, temperature, and humidity within the microclimate management system.

According to another aspect, a frame includes a siderail operable between a raised position and a lowered position. A transmitting element is coupled to an inner surface of the siderail and is configured to align with a receiving assembly to form a charging interface.

According to another aspect, a surface assembly includes a pneumatic system disposed within an interior and having a pump configured to adjust bladders between a deployed state and a non-deployed state. The pump includes a receiving element configured to selectively interact with a transmitting element to power the pump. A sensor is configured to sense pressure within the bladders.

According to another aspect of the present disclosure, a charging system for a medical facility includes a support apparatus having a frame and a siderail. The frame has a supporting surface. A surface assembly is selectively positioned on the supporting surface. A transmitting element is coupled to at least one of the frame and the siderail. A sensor assembly includes a biometric sensor that is configured to obtain biometric data of a person supported on the surface assembly. A receiving assembly is operably coupled to the sensor assembly. The receiving assembly is configured to selectively interact with the transmitting element to power the sensor assembly via a charging interface. A first locating feature is coupled to the support apparatus. A second locating feature is coupled to the surface assembly and configured to engage the first locating feature. The receiving assembly is aligned with the transmitting element to form the charging interface when the first locating feature is engaged with the second locating feature.

According to another aspect, a controller is communicatively coupled to a sensor assembly. The sensor assembly is configured to communicate biometric data to the controller. The controller is configured to communicate the biometric data to at least one of an electronic medical record and an application interface.

According to another aspect, a surface assembly includes a surface selectively coupled to a surface assembly core. A transmitting element is coupled to the surface.

According to another aspect, a biometric sensor is printed on an outer side of a surface.

According to another aspect, a surface assembly includes a surface having a top ticking and a bottom ticking. A biometric sensor is printed on a top surface of the top ticking.

According to another aspect, a first locating feature is flush with a supporting surface. A second locating feature is flush with a surface of a surface assembly.

According to another aspect, a transmitting element is coupled to a siderail when the receiving assembly is coupled to a top surface of a top ticking. The transmitting element is coupled to a supporting surface when a receiving element is coupled to a bottom surface of the top ticking.

According to another aspect, a transmitting element and a receiving element are configured to selectively interact via at least one of inductive coupling and capacitive coupling.

According to another aspect, a sensor assembly includes an interface pressure sensor. The interface pressure sensor is in communication with a controller of a support apparatus. The interface pressure sensor is configured to sense interface pressure between a patient and a surface assembly.

According to another aspect, a sensor assembly includes an identification sensor. Energy transferred via a charging interface is adjusted in response to a type of surface assembly sensed by the identification sensor.

According to another aspect, a surface assembly includes a pneumatic system having bladders. A sensor assembly includes a sensor configured to sense at least one of temperature within the surface assembly, humidity within the surface assembly, and pressure within the bladders.

According to another aspect, a charging system for a patient support apparatus includes a support apparatus having a supporting surface. A transmitting element is coupled to the support apparatus. A surface assembly is selectively positioned on the supporting surface. The surface assembly includes a pneumatic system having bladders in fluid communication with a pump. A controller is communicatively coupled to the pneumatic system. The controller is configured to selectively adjust the bladders between a deployed state and a non-deployed state. A receiving assembly is operably coupled to the pump. The receiving assembly includes a receiving element configured to selectively interact with the transmitting element via at least one of inductive coupling and capacitive coupling to power the pump.

According to another aspect, a sensor assembly is coupled to at least one bladder. The sensor assembly includes a bladder pressure sensor to sense pressure within the corresponding bladder. The sensor assembly is operably coupled to a receiving assembly.

According to another aspect, a control unit of a sensor assembly includes communication circuitry configured to communicate pressure data to a controller.

According to another aspect, a controller is configured to communicate pressure data to at least one of an electronic medical record and an application interface.

According to another aspect, a receiving assembly includes a storage feature operably coupled to a receiving element.

According to another aspect, a control unit of a receiving assembly is configured to determine a current charge level of a storage feature and communicate the current charge level to a controller. Data transfer to the controller is initiated when the current charge level reaches a predefined charge level.

According to another aspect, an interface pressure sensor is in communication with a controller. The interface pressure sensor is configured to sense a pressure between a patient and a surface assembly.

According to another aspect, a biometric sensor is operably coupled to a receiving assembly. The biometric sensor is configured to sense biometric data of the patient.

According to another aspect, a patient support charging system includes a support apparatus having a supporting surface. A transmitting element is coupled to the support apparatus. A microclimate management system is selectively positioned over the supporting surface. The microclimate management system includes a blower, a coverlet, and a spacer material within the coverlet. The blower is configured to direct air through the spacer material.

A receiving assembly is operably coupled to the blower. The receiving assembly includes a receiving element configured to selectively interact with the transmitting element via a charging interface to power the blower.

According to another aspect, a charging interface includes at least one of inductive coupling and capacitive coupling.

According to another aspect, a surface assembly is selectively positioned on a supports surface. The microclimate management system is selectively disposed on the surface assembly.

According to another aspect, a sensor assembly is coupled to at least one of a microclimate management system and a surface assembly.

According to another aspect, a charging system for a patient support apparatus includes a transmitting element coupled to a surface of a support apparatus. A controller is communicatively coupled with the transmitting element. A receiving assembly has a receiving element and a storage feature. The receiving element is configured to selectively interact with the transmitting element via at least one of capacitive coupling and inductive to power the sensor assembly. A sensor assembly is operably coupled with the receiving assembly.

According to another aspect, a support apparatus is at least one of a medical bed, a stretcher, an examination table, a surface assembly, and a support sling.

According to another aspect, a surface assembly is disposed on a support apparatus. A sensor assembly is coupled to the surface assembly and a receiving assembly.

According to another aspect, a surface assembly includes a pump operably coupled with a receiving assembly.

According to another aspect, a sensor assembly includes at least one of a biometric sensor, a bladder pressure sensor, an identification sensor, a humidity sensor, a temperature sensor, and an airflow sensor.

According to another aspect, a charging system fora support apparatus includes a surface assembly having an outer surface. Transmitting elements are coupled to the surface assembly proximate to a top surface thereof. The transmitting elements are arranged in an array. A transmission unit is operably coupled to the transmitting elements. The transmission unit is configured to selectively energize the transmitting elements. A controller is communicatively coupled to the transmission unit. The controller is configured to determine the transmitting elements to be selectively energized by the transmission unit. A sensor assembly is configured to engage a person supported on the surface assembly. The sensor assembly includes a sensor for obtaining patient data. A receiving assembly is operably coupled to the sensor assembly. The receiving assembly is configured to selectively interact with at least one of the transmitting elements to power the sensor assembly.

According to another aspect, a sensor is at least one of a biometric sensor configured to obtain biometric data and a pressure sensor configured to obtain interface pressure between the person and a surface assembly.

According to another aspect, transmitting elements are embedded in an outer surface of a surface assembly.

According to another aspect, a sensor assembly is configured to wirelessly communicate sensed data to an information system.

According to another aspect, a transmission unit selectively energizes transmitting elements in response to a location of a receiving assembly.

According to another aspect, a controller is configured to communicate with an application interface to display a graphic representative of transmitting elements on a surface assembly. The graphic is configured to distinguish transmitter indicators for the transmitting elements that are active from the transmitter indicators for the transmitting elements that are inactive.

According to another aspect, a receiving assembly includes a supercapacitor to store energy to power a sensor assembly.

According to another aspect, a patient support apparatus includes a first means for supporting a patient. The first means for supporting the patient includes a supporting surface. A means for transmitting is coupled to the first means for supporting. A second means for supporting is positioned on the supporting surface. The second means for supporting includes a cover. A means for controlling is communicatively coupled to the means for transmitting. A means for sensing is coupled to the second means for supporting. The means for sensing is configured to sense information about at least one of the second means for supporting and a person positioned on the second means for supporting. A means for charging operably coupled to the second means for supporting and the means for sensing. The means for charging includes a means for receiving configured to selectively interact with the means for transmitting via a charging interface to power the means for sensing.

Related applications, for example those listed herein, are fully incorporated by reference. Descriptions within the related applications are intended to contribute to the description of the information disclosed herein as may be relied upon by a person of ordinary skill in the art. Any changes between any of the related applications and the present disclosure are not intended to limit the description of the information disclosed herein, including the claims. Accordingly, the present application includes the description of the information disclosed herein as well as the description of the information in any or all of the related applications.

It will be understood by one having ordinary skill in the art that construction of the described disclosure and other components is not limited to any specific material. Other exemplary embodiments of the disclosure disclosed herein may be formed from a wide variety of materials, unless described otherwise herein.

For purposes of this disclosure, the term "coupled" (in all of its forms, couple, coupling, coupled, etc.) generally means the joining of two components (electrical or mechanical) directly or indirectly to one another. Such joining may be stationary in nature or movable in nature. Such joining may be achieved with the two components (electrical or mechanical) and any additional intermediate members being integrally formed as a single unitary body with one another or with the two components. Such joining may be permanent in nature or may be removable or releasable in nature unless otherwise stated.

It is also important to note that the construction and arrangement of the elements of the disclosure, as shown in the exemplary embodiments, is illustrative only. Although only a few embodiments of the present innovations have been described in detail in this disclosure, those skilled in the art who review this disclosure will readily appreciate that many modifications are possible (e.g., variations in sizes, dimensions, structures, shapes, and proportions of the various elements, values of parameters, mounting arrangements, use of materials, colors, orientations, etc.) without materially departing from the novel teachings and advantages of the subject matter recited. For example, elements shown as integrally formed may be constructed of multiple parts, or elements shown as multiple parts may be integrally formed, the operation of the interfaces may be reversed or otherwise varied, the length or width of the structures and/or members or connector or other elements of the system may be varied, the nature or number of adjustment positions provided between the elements may be varied. It should be noted that the elements and/or assemblies of the system may be constructed from any of a wide variety of materials that provide sufficient strength or durability, in any of a wide variety of colors, textures, and combinations. Accordingly, all such modifications are intended to be included within the scope of the present innovations. Other substitutions, modifications, changes, and omissions may be made in the design, operating conditions, and arrangement of the desired and other exemplary embodiments without departing from the spirit of the present innovations.

It will be understood that any described processes or steps within described processes may be combined with other disclosed processes or steps to form structures within the scope of the present disclosure. The exemplary structures and processes disclosed herein are for illustrative purposes and are not to be construed as limiting.

What is claimed is:

1. A patient support apparatus, comprising:
   a frame having a supporting surface;
   a transmitting element coupled to the frame;
   a surface assembly selectively positioned on the supporting surface, wherein the surface assembly includes a surface selectively enclosing an interior;
   a controller communicatively coupled to the transmitting element;
   a sensor assembly coupled to the surface assembly, wherein the sensor assembly includes a patient sensor configured to sense information about a person positioned on the surface assembly and an identification sensor configured to sense identification data about the surface assembly; and
   a receiving assembly operably coupled to the surface assembly and the sensor assembly, wherein the receiving assembly is configured to selectively interact with the transmitting element via a charging interface to power the sensor assembly, and wherein an amount of power transferred via the charging interface is higher when the surface assembly is a powered surface configuration than when the surface assembly is a non-powered surface configuration based on sensed identification data.

2. The patient support apparatus of claim 1, wherein the receiving assembly includes a storage feature configured as a supercapacitor operably coupled to a receiving element of the receiving assembly to store energy to power the sensor assembly.

3. The patient support apparatus of claim 1, wherein the sensor is coupled to the surface of the surface assembly and configured to sense patient information, and wherein the patient information includes at least one of heart rate, respiration rate, skin conductivity, blood surface, saturation $O_2$, and thoracic sounds.

4. The patient support apparatus of claim 1, wherein at least one of the controller and a control unit of the receiving assembly is configured to determine a coupling coefficient between the transmitting element and a receiving element of the receiving assembly.

5. The patient support apparatus of claim 4, wherein at least one of the controller and the control unit is configured to modulate a magnitude of electromagnetic fields generated between the transmitting element and the receiving element based on the coupling coefficient.

6. The patient support apparatus of claim 1, wherein the sensor is configured to sense surface information including at least one of airflow, temperature, humidity, blower speed, bladder pressure, patient immersion, and a type of surface assembly.

7. The patient support apparatus of claim 1, further comprising:
a microclimate management system operably coupled with the sensor assembly, wherein the sensor assembly is configured to sense at least one of airflow, temperature, and humidity within the microclimate management system.

8. The patient support apparatus of claim 1, wherein the surface assembly includes a pneumatic system disposed within the interior and having a pump configured to adjust bladders between a deployed state and a non-deployed state, and wherein the pump includes a receiving element of the receiving assembly configured to selectively interact with the transmitting element to power the pump, and wherein the sensor assembly is configured to sense pressure within the bladders.

9. The patient support apparatus of claim 1, wherein the frame includes a siderail, and wherein the transmitting element is coupled to the siderail, and wherein the receiving assembly includes a first receiving element proximate to a top surface of the surface assembly and a second receiving element proximate to a bottom surface of the surface assembly, and further wherein the transmitting element forms the charging interface with the first receiving element when the siderail is raised and the second receiving element when the siderail is lowered.

10. The patient support apparatus of claim 1, wherein the sensor assembly is operable between a first lower energy state and a second higher energy state, and wherein the sensor assembly is configured to communicate sensed data in the second higher energy state.

11. The patient support apparatus of claim 10, wherein the sensor assembly is configured to sense information about at least one of the person and the surface assembly when in the first lower energy state.

12. The patient support apparatus of claim 1, wherein the receiving assembly includes a control unit, and wherein at least one of the controller and the control unit is configured to modulate a magnitude of electromagnetic fields generated between the transmitting element and the receiving assembly until at least one of a minimum exposure level for the person supported on the surface assembly and a minimum energy storage level in a storage feature of the receiving assembly is reached.

13. A patient support apparatus, comprising:
a frame having a supporting surface;
a transmitting element coupled to the frame;
a surface assembly selectively positioned on the supporting surface, wherein the surface assembly includes a surface selectively enclosing an interior;
a controller communicatively coupled to the transmitting element;
a sensor assembly coupled to the surface assembly, wherein the sensor assembly includes a patient sensor configured to sense information about a person positioned on the surface assembly and an identification sensor configured to sense identification data about the surface assembly; and
a receiving assembly operably coupled to the surface assembly and the sensor assembly, wherein the receiving assembly is configured to selectively interact with the transmitting element via a charging interface to power the sensor assembly, and wherein movement of the frame changes based on sensed identification data including whether the surface assembly is a powered surface configuration or the surface assembly is a non-powered surface configuration.

14. The patient support apparatus of claim 13, wherein the powered surface configuration of the surface assembly includes a pneumatic system disposed within the interior, and wherein the pneumatic system includes a pump configured to adjust bladders between a deployed state and a non-deployed state, and wherein the pump includes a receiving element of the receiving assembly configured to selectively interact with the transmitting element to power the pump.

15. The patient support apparatus of claim 14, wherein the sensor assembly is configured to sense pressure within the bladders.

16. A patient support apparatus, comprising:
a frame having a supporting surface;
a transmitting element coupled to the frame;
a surface assembly selectively positioned on the supporting surface, wherein the surface assembly includes a surface selectively enclosing an interior;
a controller communicatively coupled to the transmitting element;
a sensor assembly coupled to the surface assembly, wherein the sensor assembly includes a sensor configured to sense information about at least one of the surface assembly and a person positioned on the surface assembly; and
a receiving assembly operably coupled to the surface assembly and the sensor assembly, wherein the receiving assembly is configured to selectively interact with the transmitting element via a charging interface to power the sensor assembly, and wherein a magnitude of electromagnetic fields generated between the transmitting element and the receiving assembly is adjusted until a minimum exposure level for a patient is reached.

17. The patient support apparatus of claim 16, wherein the receiving assembly includes a control unit, and wherein one of the controller and the control unit is configured to modulate the magnitude of electromagnetic fields generated, and further wherein modulation is configured to occur through at least one of direct communication via the charging interface and secondary communication via a communication network.

18. The patient support apparatus of claim 16, wherein the surface assembly includes an upper layer formed from a microclimate management system, and wherein the microclimate management system is operably coupled with the sensor assembly, and further wherein the sensor assembly is configured to sense at least one of airflow, temperature, and humidity within the microclimate management system.

* * * * *